United States Patent
Strom et al.

(10) Patent No.: US 10,781,248 B2
(45) Date of Patent: Sep. 22, 2020

(54) α1-ANTITRYPSIN COMPOSITIONS AND METHODS OF TREATING AUTOIMMUNE DISEASES

(71) Applicant: Beth Israel Deaconess Medical Center, Inc., Boston, MA (US)

(72) Inventors: Terry B. Strom, Brookline, MA (US); Maria Koulmanda, Brookline, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 16/166,990

(22) Filed: Oct. 22, 2018

(65) Prior Publication Data
US 2019/0276516 A1 Sep. 12, 2019

Related U.S. Application Data

(63) Continuation of application No. 15/317,136, filed as application No. PCT/US2015/035385 on Jun. 15, 2011, now abandoned.

(60) Provisional application No. 62/010,741, filed on Jun. 11, 2014.

(51) Int. Cl.
C07K 14/81 (2006.01)
C12N 15/62 (2006.01)
A61K 47/68 (2017.01)

(52) U.S. Cl.
CPC .......... *C07K 14/8125* (2013.01); *A61K 47/68* (2017.08); *C07K 2319/30* (2013.01)

(58) Field of Classification Search
CPC ............................ C07K 14/81; C07K 14/8125; C07K 2319/30; A61K 38/57; C12N 15/62
See application file for complete search history.

(56) References Cited

U.S. PATENT DOCUMENTS

| | | | | |
|---|---|---|---|---|
| 8,633,305 B2* | 1/2014 | Shapiro | ................ | A61K 31/519 435/320.1 |
| 9,938,353 B2* | 4/2018 | Dinarello | ........... | C07K 14/8125 |
| 2010/0286066 A1* | 11/2010 | Durrani | ................ | A61K 9/0078 514/20.9 |
| 2014/0147441 A1 | 5/2014 | Flier et al. | | |

FOREIGN PATENT DOCUMENTS

| | | | |
|---|---|---|---|
| WO | WO 2008/030558 | 3/2008 | |
| WO | WO 2012/087835 | 6/2012 | |
| WO | WO-2012178102 A2 * | 12/2012 | ............. C07K 16/40 |
| WO | WO 2013/003641 | 1/2013 | |
| WO | WO2013/106589 | 7/2013 | |

OTHER PUBLICATIONS

EP Office Action in European Appln. No. 15805947.7, dated Apr. 16, 2020, 9 pages.
EP Supplementary European Search Report issued in EP15805947.7 dated Oct. 25, 2017.
Koulmanda et al., "Curative and beta cell regenerative effects of alpha1-antitrypsin treatment in autoimmune diabetic NOD mice," Proc. Natl. Acad. Sci. USA, 105:16242-16247 (2008).
Niemann et al., "Isolation and Serine Protease Inhibitory Activity of the 44-Residue, C-Terminal Fragment of αl-Antitrypsin from Human Placenta," Matrix, 12:233-241 (1992).
PCT International Search Report and Written Opinion issued in PCT/US2015/035385 dated Dec. 30, 2015.
Tanaka et al., "Characterization of a 54 kDa, alpha 1-antitrypsin-like protein isolated from ascitic fluid of an endometrial cancer patient," Jpn J. Cancer Res., 82:693-700 (1991).

* cited by examiner

*Primary Examiner* — Karen Cochrane Carlson
(74) *Attorney, Agent, or Firm* — Fish & Richardson P.C.

(57) ABSTRACT

The specification provides compositions comprising chimeric proteins comprising AAT conjugated to an Fc region of an immunoglobulin. Methods for treating autoimmune disease, e.g., diabetes, e.g., Type 1 and Type 2 diabetes, are also provided.

12 Claims, 7 Drawing Sheets

Specification includes a Sequence Listing.

FIG. 1

SEQUENCE LISTING

<160> NUMBER OF SEQ ID NOS: 22

<210> SEQ ID NO 1
<211> LENGTH: 1257
<212> TYPE: DNA
<213> ORGANISM: Homo sapiens

<400> SEQUENCE: 1

```
atgccgtctt ctgtctcgtg gggcatcctc ctgctggcag gcctgtgctg cctggtccct      60
gtctccctgg ctgaggatcc ccagggagat gctgcccaga agacagatac atcccaccat     120
gatcaggatc acccaacctt caacaagatc accccccaacc tggctgagtt cgccttcagc    180
ctataccgcc agctggcaca ccagtccaac agcaccaata tcttcttctc cccagtgagc     240
atcgctacag cctttgcaat gctctccctg ggaccaagg ctgacactca cgatgaaatc       300
ctggagggcc tgaatttcaa cctcacggag attccggagg ctcagatcca tgaaggcttc     360
caggaactcc tccgtaccct caaccagcca gacagccagc tccagctgac caccggcaat     420
ggcctgttcc tcagcgaggg cctgaagcta gtggataagt ttttggagga tgttaaaaag     480
ttgtaccact cagaagcctt cactgtcaac ttcggggaca ccgaagaggc caagaaacag     540
atcaacgatt acgtggagaa gggtactcaa gggaaaattg tggatttggt caaggagctt     600
gacagagaca cagttttgc tctggtgaat tacatcttct ttaaaggcaa atgggagaga      660
ccctttgaag tcaaggacac cgaggaagag gacttccacg tggaccaggt gaccaccgtg     720
aaggtgccta tgatgaagcg tttaggcatg tttaacatcc agcactgtaa gaagctgtcc     780
agctgggtgc tgctgatgaa atacctgggc aatgccaccg ccatcttctt cctgcctgat     840
gaggggaaac tacagcacct ggaaaatgaa ctcacccacg atatcatcac caagttcctg     900
gaaaatgaag acagaaggtc tgccagctta catttaccca aactgtccat tactggaacc     960
tatgatctga agagcgtcct gggtcaactg ggcatcacta aggtcttcag caatggggct    1020
gacctctccg gggtcacaga ggaggcaccc ctgaagctct ccaaggccgt gcataaggct    1080
gtgctgacca tcgacgagaa agggactgaa gctgctgggg ccatgttttt agaggccata    1140
cccatgtcta tccccccccga ggtcaagttc aacaaaccct tgtcttcttc aatgattgaa    1200
caaaatacca gtctcccct cttcatggga aagtggtga atcccaccca aaaataa         1257
```

<210> SEQ ID NO 2
<211> LENGTH: 418
<212> TYPE: PRT
<213> ORGANISM: Homo sapiens

<400> SEQUENCE: 2

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
```

|   |   |   |   |   | 100 |   |   |   |   | 105 |   |   |   |   | 110 |   |   |
|---|---|---|---|---|---|---|---|---|---|---|---|---|---|---|---|---|---|

Glu Ala Gln Ile His Glu Gly Phe Gln Glu Leu Leu Arg Thr Leu Asn
                100                 105                 110

Gln Pro Asp Ser Gln Leu Gln Leu Thr Thr Gly Asn Gly Leu Phe Leu
115                 120                 125

Ser Glu Gly Leu Lys Leu Val Asp Lys Phe Leu Glu Asp Val Lys Lys
130                 135                 140

Leu Tyr His Ser Glu Ala Phe Thr Val Asn Phe Gly Asp Thr Glu Glu
145                 150                 155                 160

Ala Lys Lys Gln Ile Asn Asp Tyr Val Glu Lys Gly Thr Gln Gly Lys
        165                 170                 175

Ile Val Asp Leu Val Lys Glu Leu Asp Arg Asp Thr Val Phe Ala Leu
    180                 185                 190

Val Asn Tyr Ile Phe Phe Lys Gly Lys Trp Glu Arg Pro Phe Glu Val
195                 200                 205

Lys Asp Thr Glu Glu Glu Asp Phe His Val Asp Gln Val Thr Thr Val
210                 215                 220

Lys Val Pro Met Met Lys Arg Leu Gly Met Phe Asn Ile Gln His Cys
225                 230                 235                 240

Lys Lys Leu Ser Ser Trp Val Leu Leu Met Lys Tyr Leu Gly Asn Ala
        245                 250                 255

Thr Ala Ile Phe Phe Leu Pro Asp Glu Gly Lys Leu Gln His Leu Glu
    260                 265                 270

Asn Glu Leu Thr His Asp Ile Ile Thr Lys Phe Leu Glu Asn Glu Asp
275                 280                 285

Arg Arg Ser Ala Ser Leu His Leu Pro Lys Leu Ser Ile Thr Gly Thr
290                 295                 300

Tyr Asp Leu Lys Ser Val Leu Gly Gln Leu Gly Ile Thr Lys Val Phe
305                 310                 315                 320

Ser Asn Gly Ala Asp Leu Ser Gly Val Thr Glu Glu Ala Pro Leu Lys
        325                 330                 335

Leu Ser Lys Ala Val His Lys Ala Val Leu Thr Ile Asp Glu Lys Gly
    340                 345                 350

Thr Glu Ala Ala Gly Ala Met Phe Leu Glu Ala Ile Pro Met Ser Ile
355                 360                 365

Pro Pro Glu Val Lys Phe Asn Lys Pro Phe Val Phe Leu Met Ile Glu
370                 375                 380

Gln Asn Thr Lys Ser Pro Leu Phe Met Gly Lys Val Val Asn Pro Thr
385                 390                 395                 400

Gln Lys
        405                 410                 415

<210> SEQ ID NO 3
<211> LENGTH: 681
<212> TYPE: DNA
<213> ORGANISM: Homo sapiens

<400> SEQUENCE: 3
gacaaaactc acacatgccc accgtgccca gcacctgaac tcctgggggg accgtcagtc      60
ttcctcttcc ccccaaaacc caaggacacc ctcatgatct cccggacccc tgaggtcaca     120
tgcgtggtgg tggacgtgag ccacgaagac cctgaggtca agttcaactg gtacgtggac     180
ggcgtggagg tgcataatgc caagacaaag ccgcggagg agcagtacaa cagcacgtac     240
cgtgtggtca gcgtcctcac cgtcctgcac caggactggc tgaatggcaa ggagtacaag     300

```
tgcaaggtct ccaacaaagc cctcccagcc cccatcgaga aaaccatctc caaagccaaa      360
gggcagcccc gagaaccaca ggtgtacacc ctgcccccat cccgggagga gatgaccaag      420
aaccaggtca gcctgacctg cctggtcaaa ggcttctatc ccagcgacat cgccgtggag      480
tgggagagca atgggcagcc ggagaacaac tacaagacca cgcctcccgt gctggactcc      540
gacggctcct tcttcctcta cagcaagctc accgtggaca agagcaggtg gcagcagggg      600
aacgtcttct catgctccgt gatgcacgag gctctgcaca accactacac gcagaagagc      660
ctctccctgt ctccgggtaa a                                                681
```

<210> SEQ ID NO 4
<211> LENGTH: 227
<212> TYPE: PRT
<213> ORGANISM: Homo sapiens

<400> SEQUENCE: 4

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225
```

<210> SEQ ID NO 5
<211> LENGTH: 681
<212> TYPE: DNA
<213> ORGANISM: Artificial Sequence
<220> FEATURE:
<223> OTHER INFORMATION: laboratory-synthesized sequence

<400> SEQUENCE: 5

```
gacaaaactc acacatgccc accgtgccca gcacctgaac tcgagggggg accgtcagtc      60
```

```
ttcctcttcc ccccaaaacc caaggacacc ctcatgatct cccggacccc tgaggtcaca      120
tgcgtggtgg tggacgtgag ccacgaagac cctgaggtca agttcaactg gtacgtggac      180
ggcgtggagg tgcataatgc caagacaaag ccgcgggagg agcagtacaa cagcacgtac      240
cgtgtggtca gcgtcctcac cgtcctgcac caggactggc tgaatggcaa ggcgtacaag      300
ccgcgggtct ccaacaaagc cctcccagcc cccatcgaga aaaccatctc caaagccaaa      360
gggcagcccc gagaaccaca ggtgtacacc ctgcccccat cccgggagga tgaccaag       420 aaccaggtca gcctgacctg cctggtcaaa ggcttctatc ccagcgacat cgccgtggag      480
tgggagagca atgggcagcc ggagaacaac tacaagacca cgcctcccgt gctggactcc      540
gacggctcct tcttcctcta cagcaagctc accgtggaca gagcaggtg gcagcagggg      600 aacgtcttct catgctccgt gatgcacgag gctctgcaca accactacac gcagaagagc      660
ctctccctgt ctccgggtaa a                                                681
```

<210> SEQ ID NO 6
<211> LENGTH: 227
<212> TYPE: PRT
<213> ORGANISM: Artificial Sequence
<220> FEATURE:
<223> OTHER INFORMATION: laboratory-synthesized sequence

<400> SEQUENCE: 6

```
Asp Lys Thr His Thr Cys Pro Pro Cys Pro Ala Pro Glu Leu Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Ala Tyr Lys Ala Ala Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 7

<211> LENGTH: 1956
<212> TYPE: DNA
<213> ORGANISM: Artificial Sequence
<220> FEATURE:
<223> OTHER INFORMATION: laboratory-synthesized sequence

<400> SEQUENCE: 7

| | | | | | |
|---|---|---|---|---|---|
| atgtacagga | tgcaactcct | gtcttgcatt | gcactaagtc | ttgcacttgt | cacgaattcg | 60 |
| gatatcgaca | aaactcacac | atgcccaccg | tgcccagcac | ctgaactcct | gggggaccg | 120 |
| tcagtcttcc | tcttcccccc | aaaacccaag | gacaccctca | tgatctcccg | gacccctgag | 180 |
| gtcacatgcg | tggtggtgga | cgtgagccac | gaagaccctg | aggtcaagtt | caactggtac | 240 |
| gtggacggcg | tggaggtgca | taatgccaag | acaaagccgc | gggaggagca | gtacaacagc | 300 |
| acgtaccgtg | tggtcagcgt | cctcaccgtc | ctgcaccagg | actggctgaa | tggcaaggag | 360 |
| tacaagtgca | aggtctccaa | caaagccctc | ccagccccca | tcgagaaaac | catctccaaa | 420 |
| gccaaagggc | agccccgaga | accacaggtg | tacaccctgc | ccccatcccg | ggaggagatg | 480 |
| accaagaacc | aggtcagcct | gacctgcctg | gtcaaaggct | tctatcccag | cgacatcgcc | 540 |
| gtggagtggg | agagcaatgg | gcagccggag | aacaactaca | agaccacgcc | tcccgtgctg | 600 |
| gactccgacg | gctccttctt | cctctacagc | aagctcaccg | tggacaagag | caggtggcag | 660 |
| caggggaacg | tcttctcatg | ctccgtgatg | cacgaggctc | tgcacaacca | ctacacgcag | 720 |
| aagagcctct | ccctgtctcc | gggtaaacca | tggggtggag | cgggttcagg | cggaggtggc | 780 |
| tctagatctg | ctgcccagaa | gacagataca | tcccaccatg | atcaggatca | cccaaccttc | 840 |
| aacaagatca | cccccaacct | ggctgagttc | gccttcagcc | tataccgcca | gctggcacac | 900 |
| cagtccaaca | gcaccaatat | cttcttctcc | ccagtgagca | tcgctacagc | ctttgcaatg | 960 |
| ctctccctgg | gaccaaggc | tgacactcac | gatgaaatcc | tggagggcct | gaatttcaac | 1020 |
| ctcacggaga | ttccggaggc | tcagatccat | gaaggcttcc | aggaactcct | ccgtaccctc | 1080 |
| aaccagccag | acagccagct | ccagctgacc | accggcaatg | gcctgttcct | cagcgagggc | 1140 |
| ctgaagctag | tggataagtt | tttggaggat | gttaaaaagt | gtaccactc | agaagccttc | 1200 |
| actgtcaact | cggggacac | cgaagaggcc | aagaaacaga | tcaacgatta | cgtggagaag | 1260 |
| ggtactcaag | ggaaaattgt | ggatttggtc | aaggagcttg | acagagacac | agttttgct | 1320 |
| ctggtgaatt | acatcttctt | taaaggcaaa | tgggagagac | cctttgaagt | caaggacacc | 1380 |
| gaggaagagg | acttccacgt | ggaccaggtg | accaccgtga | aggtgcctat | gatgaagcgt | 1440 |
| ttaggcatgt | ttaacatcca | gcactgtaag | aagctgtcca | gctgggtgct | gctgatgaaa | 1500 |
| tacctgggca | atgccaccgc | catcttcttc | ctgcctgatg | aggggaaact | acagcacctg | 1560 |
| gaaaatgaac | tcacccacga | tatcatcacc | aagttcctgg | aaaatgaaga | cagaaggtct | 1620 |
| gccagcttac | atttacccaa | actgtccatt | actggaacct | atgatctgaa | gagcgtcctg | 1680 |
| ggtcaactgg | gcatcactaa | ggtcttcagc | aatgggcctg | acctctccgg | ggtcacagag | 1740 |
| gaggcacccc | tgaagctctc | caaggccgtg | cataaggctg | tgctgaccat | cgacgagaaa | 1800 |
| gggactgaag | ctgctgggc | catgttttta | gaggccatac | ccatgtctat | cccccccgag | 1860 |
| gtcaagttca | acaaaccctt | tgtcttctta | atgattgaac | aaaataccaa | gtctcccctc | 1920 |
| ttcatgggaa | aagtggtgaa | tcccacccaa | aaataa | | | 1956 |

<210> SEQ ID NO 8
<211> LENGTH: 651
<212> TYPE: PRT
<213> ORGANISM: Artificial Sequence
<220> FEATURE:
<223> OTHER INFORMATION: laboratory-synthesized sequence

<400> SEQUENCE: 8

```
Met Tyr Arg Met Gln Leu Leu Ser Cys Ile Ala Leu Ser Leu Ala Leu
1               5                   10                  15

Val Thr Asn Ser Asp Ile Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys Pro Trp Gly Gly Gly Gly Ser
                245                 250                 255

Gly Gly Gly Gly Ser Arg Ser Ala Ala Gln Lys Thr Asp Thr Ser His
            260                 265                 270

His Asp Gln Asp His Pro Thr Phe Asn Lys Ile Thr Pro Asn Leu Ala
        275                 280                 285

Glu Phe Ala Phe Ser Leu Tyr Arg Gln Leu Ala His Gln Ser Asn Ser
    290                 295                 300

Thr Asn Ile Phe Phe Ser Pro Val Ser Ile Ala Thr Ala Phe Ala Met
305                 310                 315                 320

Leu Ser Leu Gly Thr Lys Ala Asp Thr His Asp Glu Ile Leu Glu Gly
                325                 330                 335

Leu Asn Phe Asn Leu Thr Glu Ile Pro Glu Ala Gln Ile His Glu Gly
            340                 345                 350

Phe Gln Glu Leu Leu Arg Thr Leu Asn Gln Pro Asp Ser Gln Leu Gln
        355                 360                 365

Leu Thr Thr Gly Asn Gly Leu Phe Leu Ser Glu Gly Leu Lys Leu Val
    370                 375                 380

Asp Lys Phe Leu Glu Asp Val Lys Lys Leu Tyr His Ser Glu Ala Phe
385                 390                 395                 400
```

Thr Val Asn Phe Gly Asp Thr Glu Glu Ala Lys Lys Gln Ile Asn Asp
            405                 410                 415

Tyr Val Glu Lys Gly Thr Gln Gly Lys Ile Val Asp Leu Val Lys Glu
            420                 425                 430

Leu Asp Arg Asp Thr Val Phe Ala Leu Val Asn Tyr Ile Phe Phe Lys
            435                 440                 445

Gly Lys Trp Glu Arg Pro Phe Glu Val Lys Asp Thr Glu Glu Glu Asp
            450                 455                 460

Phe His Val Asp Gln Val Thr Thr Val Lys Val Pro Met Met Lys Arg
465                 470                 475                 480

Leu Gly Met Phe Asn Ile Gln His Cys Lys Lys Leu Ser Ser Trp Val
            485                 490                 495

Leu Leu Met Lys Tyr Leu Gly Asn Ala Thr Ala Ile Phe Phe Leu Pro
            500                 505                 510

Asp Glu Gly Lys Leu Gln His Leu Glu Asn Glu Leu Thr His Asp Ile
            515                 520                 525

Ile Thr Lys Phe Leu Glu Asn Glu Asp Arg Arg Ser Ala Ser Leu His
        530                 535                 540

Leu Pro Lys Leu Ser Ile Thr Gly Thr Tyr Asp Leu Lys Ser Val Leu
545                 550                 555                 560

Gly Gln Leu Gly Ile Thr Lys Val Phe Ser Asn Gly Ala Asp Leu Ser
            565                 570                 575

Gly Val Thr Glu Glu Ala Pro Leu Lys Leu Ser Lys Ala Val His Lys
            580                 585                 590

Ala Val Leu Thr Ile Asp Glu Lys Gly Thr Glu Ala Ala Gly Ala Met
            595                 600                 605

Phe Leu Glu Ala Ile Pro Met Ser Ile Pro Pro Glu Val Lys Phe Asn
            610                 615                 620

Lys Pro Phe Val Phe Leu Met Ile Glu Gln Asn Thr Lys Ser Pro Leu
625                 630                 635                 640

Phe Met Gly Lys Val Val Asn Pro Thr Gln Lys
            645                 650

<210> SEQ ID NO 9
<211> LENGTH: 1980
<212> TYPE: DNA
<213> ORGANISM: Artificial Sequence
<220> FEATURE:
<223> OTHER INFORMATION: laboratory-synthesized sequence

<400> SEQUENCE: 9

| | |
|---|---|
| atgccgtctt ctgtctcgtg gggcatcctc ctgctggcag gcctgtgctg cctggtccct | 60 |
| gtctccctgg ctgaggatcc ccagggagat gctgcccaga agacagatac atcccaccat | 120 |
| gatcaggatc acccaacctt caacaagatc accccaacc tggctgagtt cgccttcagc | 180 |
| ctataccgcc agctggcaca ccagtccaac agcaccaata tcttcttctc cccagtgagc | 240 |
| atcgctacag cctttgcaat gctctccctg ggaccaagg ctgacactca cgatgaaatc | 300 |
| ctggagggcc tgaatttcaa cctcacggag attccggagg ctcagatcca tgaaggcttc | 360 |
| caggaactcc tccgtaccct caaccagcca gacagccagc tccagctgac caccggcaat | 420 |
| ggcctgttcc tcagcgaggg cctgaagcta gtggataagt ttttggagga tgttaaaaag | 480 |
| ttgtaccact cagaagcctt cactgtcaac ttcgggaca ccgaagaggc caagaaacag | 540 |
| atcaacgatt acgtggagaa gggtactcaa gggaaaattg tggatttggt caaggagctt | 600 |

-continued

```
gacagagaca cagttttttgc tctggtgaat tacatcttct ttaaaggcaa atgggagaga    660
cccctttgaag tcaaggacac cgaggaagag gacttccacg tggaccaggt gaccaccgtg    720
aaggtgcctta tgatgaagcg tttaggcatg tttaacatcc agcactgtaa gaagctgtcc    780
agctgggtgc tgctgatgaa ataccctggc aatgccaccg ccatcttctt cctgcctgat    840
gaggggaaac tacagcacct ggaaaatgaa ctcacccacg atatcatcac caagttcctg    900
gaaaatgaag acagaaggtc tgccagctta catttaccca aactgtccat tactggaacc    960
tatgatctga gagcgtcct gggtcaactg ggcatcacta aggtcttcag caatggggct   1020
gacctctccg gggtcacaga ggaggcaccc ctgaagctct ccaaggccgt gcataaggct   1080
gtgctgacca tcgacgagaa agggactgaa gctgctgggg ccatgttttt agaggccata   1140
cccatgtcta tcccccccga ggtcaagttc aacaaaccct ttgtcttctt aatgattgaa   1200
caaaatacca agtctcccct cttcatggga aaagtggtga atcccaccca aaaaccatgg   1260
agaggtccta cgatcaagcc ctgcccgcct agatctgaca aaactcacac atgcccaccg   1320
tgcccagcac ctgaactcct ggggggaccg tcagtcttcc tcttccccc aaaacccaag   1380
gacaccctca tgatctcccg gacccctgag gtcacatgcg tggtggtgga cgtgagccac   1440
gaagaccctg aggtcaagtt caactggtac gtggacggcg tggaggtgca taatgccaag   1500
acaaagccgc gggaggagca gtacaacagc acgtaccgtg tggtcagcgt cctcaccgtc   1560
ctgcaccagg actggctgaa tggcaaggag tacaagtgca aggtctccaa caaagccctc   1620
ccagccccca tcgagaaaac catctccaaa gccaagggc agccccgaga accacaggtg   1680
tacaccctgc ccccatcccg ggaggagatg accaagaacc aggtcagcct gacctgcctg   1740
gtcaaaggct tctatcccag cgacatcgcc gtggagtggg agagcaatgg gcagccggag   1800
aacaactaca agaccacgcc tcccgtgctg gactccgacg gctccttctt cctctacagc   1860
aagctcaccg tggacaagag caggtggcag caggggaacg tcttctcatg ctccgtgatg   1920
cacgaggctc tgcacaacca ctacacgcag aagagcctct ccctgtctcc gggtaaataa   1980
```

<210> SEQ ID NO 10
<211> LENGTH: 659
<212> TYPE: PRT
<213> ORGANISM: Artificial Sequence
<220> FEATURE:
<223> OTHER INFORMATION: laboratory-synthesized sequence

<400> SEQUENCE: 10

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125
```

```
Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
                180                 185                 190

Ile Val Asp Leu Val Lys Glu Leu Asp Arg Asp Thr Val Phe Ala Leu
            195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
                260                 265                 270

Thr Ala Ile Phe Phe Leu Pro Asp Glu Gly Lys Leu Gln His Leu Glu
            275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
    355                 360                 365

Thr Glu Ala Ala Gly Ala Met Phe Leu Glu Ala Ile Pro Met Ser Ile
370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys Pro Trp Arg Gly Pro Thr Ile Lys Pro Cys Pro Pro Arg Ser
            420                 425                 430

Asp Lys Thr His Thr Cys Pro Pro Cys Pro Ala Pro Glu Leu Leu Gly
    435                 440                 445

Gly Pro Ser Val Phe Leu Phe Pro Pro Lys Pro Lys Asp Thr Leu Met
450                 455                 460

Ile Ser Arg Thr Pro Glu Val Thr Cys Val Val Val Asp Val Ser His
465                 470                 475                 480

Glu Asp Pro Glu Val Lys Phe Asn Trp Tyr Val Asp Gly Val Glu Val
                485                 490                 495

His Asn Ala Lys Thr Lys Pro Arg Glu Glu Gln Tyr Asn Ser Thr Tyr
            500                 505                 510

Arg Val Val Ser Val Leu Thr Val Leu His Gln Asp Trp Leu Asn Gly
    515                 520                 525

Lys Glu Tyr Lys Cys Lys Val Ser Asn Lys Ala Leu Pro Ala Pro Ile
530                 535                 540
```

| Glu | Lys | Thr | Ile | Ser | Lys | Ala | Lys | Gly | Gln | Pro | Arg | Glu | Pro | Gln | Val |
|---|---|---|---|---|---|---|---|---|---|---|---|---|---|---|---|
| 545 | | | | 550 | | | | | 555 | | | | | 560 | |

| Tyr | Thr | Leu | Pro | Pro | Ser | Arg | Glu | Glu | Met | Thr | Lys | Asn | Gln | Val | Ser |
|---|---|---|---|---|---|---|---|---|---|---|---|---|---|---|---|
| | | | | 565 | | | | | 570 | | | | | 575 | |

| Leu | Thr | Cys | Leu | Val | Lys | Gly | Phe | Tyr | Pro | Ser | Asp | Ile | Ala | Val | Glu |
|---|---|---|---|---|---|---|---|---|---|---|---|---|---|---|---|
| | | | 580 | | | | | 585 | | | | | 590 | | |

| Trp | Glu | Ser | Asn | Gly | Gln | Pro | Glu | Asn | Asn | Tyr | Lys | Thr | Thr | Pro | Pro |
|---|---|---|---|---|---|---|---|---|---|---|---|---|---|---|---|
| | | | 595 | | | | | 600 | | | | | 605 | | |

| Val | Leu | Asp | Ser | Asp | Gly | Ser | Phe | Phe | Leu | Tyr | Ser | Lys | Leu | Thr | Val |
|---|---|---|---|---|---|---|---|---|---|---|---|---|---|---|---|
| | 610 | | | | | 615 | | | | | 620 | | | | |

| Asp | Lys | Ser | Arg | Trp | Gln | Gln | Gly | Asn | Val | Phe | Ser | Cys | Ser | Val | Met |
|---|---|---|---|---|---|---|---|---|---|---|---|---|---|---|---|
| 625 | | | | | 630 | | | | | 635 | | | | | 640 |

| His | Glu | Ala | Leu | His | Asn | His | Tyr | Thr | Gln | Lys | Ser | Leu | Ser | Leu | Ser |
|---|---|---|---|---|---|---|---|---|---|---|---|---|---|---|---|
| | | | | 645 | | | | | 650 | | | | | 655 | |

Pro Gly Lys

<210> SEQ ID NO 11
<211> LENGTH: 1995
<212> TYPE: DNA
<213> ORGANISM: Artificial Sequence
<220> FEATURE:
<223> OTHER INFORMATION: laboratory-synthesized sequence

<400> SEQUENCE: 11

| atgccgtctt | ctgtctcgtg | gggcatcctc | ctgctggcag | gcctgtgctg | cctggtccct | 60 |
|---|---|---|---|---|---|---|
| gtctccctgg | ctgaggatcc | ccagggagat | gctgcccaga | agacagatac | atcccaccat | 120 |
| gatcaggatc | acccaacctt | caacaagatc | accccccaacc | tggctgagtt | cgccttcagc | 180 |
| ctataccgcc | agctggcaca | ccagtccaac | agcaccaata | tcttcttctc | cccagtgagc | 240 |
| atcgctacag | cctttgcaat | gctctccctg | gggaccaagg | ctgacactca | cgatgaaatc | 300 |
| ctggagggcc | tgaatttcaa | cctcacggag | attccgagg | ctcagatcca | tgaaggcttc | 360 |
| caggaactcc | tccgtaccct | caaccagcca | gacagccagc | tccagctgac | caccggcaat | 420 |
| ggcctgttcc | tcagcgaggg | cctgaagcta | gtggataagt | ttttggagga | tgttaaaaag | 480 |
| ttgtaccact | cagaagcctt | cactgtcaac | ttcggggaca | ccgaagaggc | caagaaacag | 540 |
| atcaacgatt | acgtggagaa | gggtactcaa | gggaaaattg | tggatttggt | caaggagctt | 600 |
| gacagagaca | cagttttttgc | tctggtgaat | tacatcttct | ttaaaggcaa | atgggagaga | 660 |
| ccctttgaag | tcaaggacac | cgaggaagag | gacttccacg | tggaccaggt | gaccaccgtg | 720 |
| aaggtgccta | tgatgaagcg | tttaggcatg | tttaacatcc | agcactgtaa | gaagctgtcc | 780 |
| agctgggtgc | tgctgatgaa | atacctgggc | aatgccaccg | ccatcttctt | cctgcctgat | 840 |
| gaggggaaac | tacagcacct | ggaaaatgaa | ctcacccacg | atatcatcac | caagttcctg | 900 |
| gaaaatgaag | acagaaggtc | tgccagctta | catttaccca | aactgtccat | tactggaacc | 960 |
| tatgatctga | gagcgtcct | gggtcaactg | gcatcacta | aggtcttcag | caatgggct | 1020 |
| gacctctccg | gggtcacaga | ggaggcaccc | ctgaagctct | ccaaggccgt | gcataaggct | 1080 |
| gtgctgacca | tcgacgagaa | agggactgaa | gctgctgggg | ccatgttttt | agaggccata | 1140 |
| cccatgtcta | tccccccga | ggtcaagttc | aacaaacct | ttgtcttctt | aatgattgaa | 1200 |
| caaaatacca | gtctccccct | cttcatggga | aaagtggtga | atcccaccca | aaaaccatgg | 1260 |
| ggtggaggcg | gttcaagagg | tcctacgatc | aagccctgcc | cgcctagatc | tgacaaaact | 1320 |
| cacacatgcc | caccgtgccc | agcacctgaa | ctcctggggg | gaccgtcagt | cttcctcttc | 1380 |

```
ccccaaaac  caaggacac   cctcatgatc  tcccggaccc  ctgaggtcac  atgcgtggtg   1440
gtggacgtga  gccacgaaga  ccctgaggtc  aagttcaact  ggtacgtgga  cggcgtggag   1500
gtgcataatg  ccaagacaaa  gccgcgggag  gagcagtaca  acagcacgta  ccgtgtggtc   1560
agcgtcctca  ccgtcctgca  ccaggactgg  ctgaatggca  aggagtacaa  gtgcaaggtc   1620
tccaacaaag  ccctcccagc  ccccatcgag  aaaaccatct  ccaaagccaa  agggcagccc   1680
cgagaaccac  aggtgtacac  cctgccccca  tcccgggagg  agatgaccaa  gaaccaggtc   1740
agcctgacct  gcctggtcaa  aggcttctat  cccagcgaca  tcgccgtgga  gtgggagagc   1800
aatgggcagc  cggagaacaa  ctacaagacc  acgcctcccg  tgctggactc  cgacggctcc   1860
ttcttcctct  acagcaagct  caccgtggac  aagagcaggt  ggcagcaggg  gaacgtcttc   1920
tcatgctccg  tgatgcacga  ggctctgcac  aaccactaca  cgcagaagag  cctctccctg   1980
tctccgggta  ataa                                                          1995
```

<210> SEQ ID NO 12
<211> LENGTH: 664
<212> TYPE: PRT
<213> ORGANISM: Artificial Sequence
<220> FEATURE:
<223> OTHER INFORMATION: laboratory-synthesized sequence

<400> SEQUENCE: 12

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255
```

```
Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
            275                 280                 285

Asn Glu Leu Thr His Asp Ile Ile Thr Lys Phe Leu Glu Asn Glu Asp
            290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
            325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
            355                 360                 365

Thr Glu Ala Ala Gly Ala Met Phe Leu Glu Ala Ile Pro Met Ser Ile
            370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
            405                 410                 415

Gln Lys Pro Trp Gly Gly Gly Gly Ser Arg Gly Pro Thr Ile Lys Pro
            420                 425                 430

Cys Pro Pro Arg Ser Asp Lys Thr His Thr Cys Pro Pro Cys Pro Ala
            435                 440                 445

Pro Glu Leu Leu Gly Gly Pro Ser Val Phe Leu Phe Pro Pro Lys Pro
            450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
            485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
            515                 520                 525

Asp Trp Leu Asn Gly Lys Glu Tyr Lys Cys Lys Val Ser Asn Lys Ala
            530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
            565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
            595                 600                 605

Lys Thr Thr Pro Pro Val Leu Asp Ser Asp Gly Ser Phe Phe Leu Tyr
            610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
            645                 650                 655

Ser Leu Ser Leu Ser Pro Gly Lys
            660
```

<210> SEQ ID NO 13
<211> LENGTH: 1956
<212> TYPE: DNA
<213> ORGANISM: Artificial Sequence
<220> FEATURE:
<223> OTHER INFORMATION: laboratory-synthesized sequence

<400> SEQUENCE: 13

```
atgtacagga tgcaactcct gtcttgcatt gcactaagtc ttgcacttgt cacgaattcg      60
gatatcgaca aaactcacac atgcccaccg tgcccagcac ctgaactcga ggggggaccg     120
tcagtcttcc tcttcccccc aaaacccaag gacaccctca tgatctcccg gacccctgag     180
gtcacatgcg tggtggtgga cgtgagccac gaagaccctg aggtcaagtt caactggtac     240
gtggacggcg tggaggtgca taatgccaag acaaagccgc gggaggagca gtacaacagc     300
acgtaccgtg tggtcagcgt cctcaccgtc ctgcaccagg actggctgaa tggcaaggcg     360
tacaaggccg cggtctccaa caaagccctc ccagccccca tcgagaaaac catctccaaa     420
gccaaagggc agccccgaga accacaggtg tacaccctgc ccccatcccg ggaggagatg     480
accaagaacc aggtcagcct gacctgcctg gtcaaaggct tctatcccag cgacatcgcc     540
gtggagtggg agagcaatgg gcagccggag aacaactaca agaccacgcc tcccgtgctg     600
gactccgacg gctccttctt cctctacagc aagctcaccg tggacaagag caggtggcag     660
caggggaacg tcttctcatg ctccgtgatg cacgaggctc tgcacaacca ctacacgcag     720
aagagcctct ccctgtctcc gggtaaacca tggggtggag gcggttcagg cggaggtggc     780
tctagatctg ctgcccagaa gacagataca tcccaccatg atcaggatca cccaaccttc     840
aacaagatca cccccaacct ggctgagttc gccttcagcc tataccgcca gctggcacac     900
cagtccaaca gcaccaatat cttcttctcc ccagtgagca tcgctacagc ctttgcaatg     960
ctctccctgg gaccaaggc tgacactcac gatgaaatcc tggagggcct gaatttcaac    1020
ctcacggaga ttccggaggc tcagatccat gaaggcttcc aggaactcct ccgtaccctc    1080
aaccagccag acagccagct ccagctgacc accggcaatg gcctgttcct cagcgagggc    1140
ctgaagctag tggataagtt tttggaggat gttaaaaagt tgtaccactc agaagccttc    1200
actgtcaact cggggacac cgaagaggcc aagaaacaga tcaacgatta cgtggagaag    1260
ggtactcaag ggaaaattgt ggatttggtc aaggagcttg acagagacac agtttttgct    1320
ctggtgaatt acatcttctt taaaggcaaa tgggagagac cctttgaagt caaggacacc    1380
gaggaagagg acttccacgt ggaccaggtg accaccgtga aggtgcctat gatgaagcgt    1440
ttaggcatgt ttaacatcca gcactgtaag aagctgtcca gctgggtgct gctgatgaaa    1500
tacctgggca atgccaccgc catcttcttc ctgcctgatg aggggaaact acagcacctg    1560
gaaaatgaac tcacccacga tatcatcacc aagttcctgg aaaatgaaga cagaaggtct    1620
gccagcttac atttacccaa actgtccatt actggaacct atgatctgaa gagcgtcctg    1680
ggtcaactgg gcatcactaa ggtcttcagc aatgggctga acctctccgg ggtcacagag    1740
gaggcacccc tgaagctctc caaggccgtg cataaggctg tgctgaccat cgacgagaaa    1800
gggactgaag ctgctgggc catgtttta gaggccatac ccatgtctat ccccccgag    1860
gtcaagttca acaaaccctt tgtcttctta atgattgaac aaaataccaa gtctcccctc    1920
ttcatgggaa agtggtgaa tcccacccaa aaataa                              1956
```

<210> SEQ ID NO 14
<211> LENGTH: 651

```
<212> TYPE: PRT
<213> ORGANISM: Artificial Sequence
<220> FEATURE:
<223> OTHER INFORMATION: laboratory-synthesized sequence

<400> SEQUENCE: 14

Met Tyr Arg Met Gln Leu Leu Ser Cys Ile Ala Leu Ser Leu Ala Leu
1               5                   10                  15

Val Thr Asn Ser Asp Ile Asp Lys Thr His Thr Cys Pro Pro Cys Pro
            20                  25                  30

Ala Pro Glu Leu Glu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Ala Tyr Lys Ala Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys Pro Trp Gly Gly Gly Gly Ser
                245                 250                 255

Gly Gly Gly Gly Ser Arg Ser Ala Ala Gln Lys Thr Asp Thr Ser His
            260                 265                 270

His Asp Gln Asp His Pro Thr Phe Asn Lys Ile Thr Pro Asn Leu Ala
        275                 280                 285

Glu Phe Ala Phe Ser Leu Tyr Arg Gln Leu Ala His Gln Ser Asn Ser
    290                 295                 300

Thr Asn Ile Phe Phe Ser Pro Val Ser Ile Ala Thr Ala Phe Ala Met
305                 310                 315                 320

Leu Ser Leu Gly Thr Lys Ala Asp Thr His Asp Glu Ile Leu Glu Gly
                325                 330                 335

Leu Asn Phe Asn Leu Thr Glu Ile Pro Glu Ala Gln Ile His Glu Gly
            340                 345                 350

Phe Gln Glu Leu Leu Arg Thr Leu Asn Gln Pro Asp Ser Gln Leu Gln
        355                 360                 365

Leu Thr Thr Gly Asn Gly Leu Phe Leu Ser Glu Gly Leu Lys Leu Val
    370                 375                 380
```

Asp Lys Phe Leu Glu Asp Val Lys Lys Leu Tyr His Ser Glu Ala Phe
385                 390                 395                 400

Thr Val Asn Phe Gly Asp Thr Glu Glu Ala Lys Lys Gln Ile Asn Asp
            405                 410                 415

Tyr Val Glu Lys Gly Thr Gln Gly Lys Ile Val Asp Leu Val Lys Glu
        420                 425                 430

Leu Asp Arg Asp Thr Val Phe Ala Leu Val Asn Tyr Ile Phe Phe Lys
    435                 440                 445

Gly Lys Trp Glu Arg Pro Phe Glu Val Lys Asp Thr Glu Glu Glu Asp
450                 455                 460

Phe His Val Asp Gln Val Thr Thr Val Lys Val Pro Met Met Lys Arg
465                 470                 475                 480

Leu Gly Met Phe Asn Ile Gln His Cys Lys Lys Leu Ser Ser Trp Val
            485                 490                 495

Leu Leu Met Lys Tyr Leu Gly Asn Ala Thr Ala Ile Phe Phe Leu Pro
        500                 505                 510

Asp Glu Gly Lys Leu Gln His Leu Glu Asn Glu Leu Thr His Asp Ile
    515                 520                 525

Ile Thr Lys Phe Leu Glu Asn Glu Asp Arg Arg Ser Ala Ser Leu His
530                 535                 540

Leu Pro Lys Leu Ser Ile Thr Gly Thr Tyr Asp Leu Lys Ser Val Leu
545                 550                 555                 560

Gly Gln Leu Gly Ile Thr Lys Val Phe Ser Asn Gly Ala Asp Leu Ser
            565                 570                 575

Gly Val Thr Glu Glu Ala Pro Leu Lys Leu Ser Lys Ala Val His Lys
        580                 585                 590

Ala Val Leu Thr Ile Asp Glu Lys Gly Thr Glu Ala Ala Gly Ala Met
    595                 600                 605

Phe Leu Glu Ala Ile Pro Met Ser Ile Pro Pro Glu Val Lys Phe Asn
610                 615                 620

Lys Pro Phe Val Phe Leu Met Ile Glu Gln Asn Thr Lys Ser Pro Leu
625                 630                 635                 640

Phe Met Gly Lys Val Val Asn Pro Thr Gln Lys
            645                 650

<210> SEQ ID NO 15
<211> LENGTH: 1980
<212> TYPE: DNA
<213> ORGANISM: Artificial Sequence
<220> FEATURE:
<223> OTHER INFORMATION: laboratory-synthesized sequence

<400> SEQUENCE: 15
atgccgtctt ctgtctcgtg gggcatcctc ctgctggcag gcctgtgctg cctggtccct     60
gtctccctgg ctgaggatcc ccagggagat gctgcccaga agacagatac atcccaccat    120
gatcaggatc acccaacctt caacaagatc acccccaacc tggctgagtt cgccttcagc    180
ctataccgcc agctggcaca ccagtccaac agcaccaata tcttcttctc cccagtgagc    240
atcgctacag cctttgcaat gctctcccta gggaccaagg ctgacactca cgatgaaatc    300
ctggagggcc tgaatttcaa cctcacggag attccgaggg ctcagatcca tgaaggcttc    360
caggaactcc tccgtaccct caaccagcca gacagccagc tccagctgac caccggcaat    420
ggcctgttcc tcagcgaggg cctgaagcta gtggataagt ttttggagga tgttaaaaag    480
ttgtaccact cagaagcctt cactgtcaac ttcggggaca ccgaagaggc caagaaacag    540

```
atcaacgatt acgtggagaa gggtactcaa gggaaaattg tggatttggt caaggagctt    600
gacagagaca cagttttttgc tctggtgaat tacatcttct ttaaaggcaa atgggagaga   660
cccctttgaag tcaaggacac cgaggaagag gacttccacg tggaccaggt gaccaccgtg   720
aaggtgccta tgatgaagcg tttaggcatg tttaacatcc agcactgtaa gaagctgtcc    780
agctgggtgc tgctgatgaa atacctgggc aatgccaccg ccatcttctt cctgcctgat    840
gagggggaaac tacagcacct ggaaaatgaa ctcacccacg atatcatcac caagttcctg   900
gaaaatgaag acagaaggtc tgccagctta catttaccca aactgtccat tactggaacc    960
tatgatctga gagcgtcctg ggtcaactgg gcatcacta aggtcttcag caatgggggct  1020
gacctctccg gggtcacaga ggaggcaccc ctgaagctct ccaaggccgt gcataaggct   1080
gtgctgacca tcgacgagaa agggactgaa gctgctgggg ccatgttttt agaggccata   1140
cccatgtcta tccccccccga ggtcaagttc aacaaaccct ttgtcttctt aatgattgaa   1200
caaaatacca agtctcccct cttcatggga aaagtggtga atcccaccca aaaaccatgg   1260
agaggtccta cgatcaagcc ctgcccgcct agatctgaca aaactcacac atgcccaccg   1320
tgcccagcac ctgaactcga ggggggaccg tcagtcttcc tcttcccccc aaaacccaag   1380
gacaccctca tgatctcccg gacccctgag gtcacatgcg tggtggtgga cgtgagccac   1440
gaagaccctg aggtcaagtt caactggtac gtggacggcg tggaggtgca taatgccaag   1500
acaaagccgc gggaggagca gtacaacagc acgtaccgtg tggtcagcgt cctcaccgtc   1560
ctgcaccagg actggctgaa tggcaaggcg tacaaggccg cggtctccaa caaagccctc   1620
ccagccccca tcgagaaaac catctccaaa gccaaagggc agccccgaga accacaggtg   1680
tacaccctgc cccatcccg ggaggagatg accaagaacc aggtcagcct gacctgcctg   1740
gtcaaaggct tctatcccag cgacatcgcc gtggagtggg agagcaatgg gcagccggag   1800
aacaactaca agaccacgcc tcccgtgctg gactccgacg gctccttctt cctctacagc   1860
aagctcaccg tggacaagag caggtggcag caggggaacg tcttctcatg ctccgtgatg   1920
cacgaggctc tgcacaacca ctacacgcag aagagcctct ccctgtctcc gggtaaatga   1980
```

<210> SEQ ID NO 16
<211> LENGTH: 659
<212> TYPE: PRT
<213> ORGANISM: Artificial Sequence
<220> FEATURE:
<223> OTHER INFORMATION: laboratory-synthesized sequence

<400> SEQUENCE: 16

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110
```

-continued

```
Glu Ala Gln Ile His Glu Gly Phe Gln Glu Leu Leu Arg Thr Leu Asn
            115                 120                 125
Gln Pro Asp Ser Gln Leu Gln Leu Thr Thr Gly Asn Gly Leu Phe Leu
        130                 135                 140
Ser Glu Gly Leu Lys Leu Val Asp Lys Phe Leu Glu Asp Val Lys Lys
145                 150                 155                 160
Leu Tyr His Ser Glu Ala Phe Thr Val Asn Phe Gly Asp Thr Glu Glu
                165                 170                 175
Ala Lys Lys Gln Ile Asn Asp Tyr Val Glu Lys Gly Thr Gln Gly Lys
            180                 185                 190
Ile Val Asp Leu Val Lys Glu Leu Asp Arg Asp Thr Val Phe Ala Leu
        195                 200                 205
Val Asn Tyr Ile Phe Phe Lys Gly Lys Trp Glu Arg Pro Phe Glu Val
210                 215                 220
Lys Asp Thr Glu Glu Glu Asp Phe His Val Asp Gln Val Thr Thr Val
225                 230                 235                 240
Lys Val Pro Met Met Lys Arg Leu Gly Met Phe Asn Ile Gln His Cys
                245                 250                 255
Lys Lys Leu Ser Ser Trp Val Leu Leu Met Lys Tyr Leu Gly Asn Ala
            260                 265                 270
Thr Ala Ile Phe Phe Leu Pro Asp Glu Gly Lys Leu Gln His Leu Glu
        275                 280                 285
Asn Glu Leu Thr His Asp Ile Ile Thr Lys Phe Leu Glu Asn Glu Asp
290                 295                 300
Arg Arg Ser Ala Ser Leu His Leu Pro Lys Leu Ser Ile Thr Gly Thr
305                 310                 315                 320
Tyr Asp Leu Lys Ser Val Leu Gly Gln Leu Gly Ile Thr Lys Val Phe
                325                 330                 335
Ser Asn Gly Ala Asp Leu Ser Gly Val Thr Glu Glu Ala Pro Leu Lys
            340                 345                 350
Leu Ser Lys Ala Val His Lys Ala Val Leu Thr Ile Asp Glu Lys Gly
        355                 360                 365
Thr Glu Ala Ala Gly Ala Met Phe Leu Glu Ala Ile Pro Met Ser Ile
370                 375                 380
Pro Pro Glu Val Lys Phe Asn Lys Pro Phe Val Phe Leu Met Ile Glu
385                 390                 395                 400
Gln Asn Thr Lys Ser Pro Leu Phe Met Gly Lys Val Val Asn Pro Thr
                405                 410                 415
Gln Lys Pro Trp Arg Gly Pro Thr Ile Lys Pro Cys Pro Pro Arg Ser
            420                 425                 430
Asp Lys Thr His Thr Cys Pro Pro Cys Pro Ala Pro Glu Leu Glu Gly
        435                 440                 445
Gly Pro Ser Val Phe Leu Phe Pro Pro Lys Pro Lys Asp Thr Leu Met
450                 455                 460
Ile Ser Arg Thr Pro Glu Val Thr Cys Val Val Val Asp Val Ser His
465                 470                 475                 480
Glu Asp Pro Glu Val Lys Phe Asn Trp Tyr Val Asp Gly Val Glu Val
                485                 490                 495
His Asn Ala Lys Thr Lys Pro Arg Glu Glu Gln Tyr Asn Ser Thr Tyr
            500                 505                 510
Arg Val Val Ser Val Leu Thr Val Leu His Gln Asp Trp Leu Asn Gly
        515                 520                 525
Lys Ala Tyr Lys Ala Ala Val Ser Asn Lys Ala Leu Pro Ala Pro Ile
```

```
                530             535             540
Glu Lys Thr Ile Ser Lys Ala Lys Gly Gln Pro Arg Glu Pro Gln Val
545                 550                 555                 560

Tyr Thr Leu Pro Pro Ser Arg Glu Glu Met Thr Lys Asn Gln Val Ser
                565                 570                 575

Leu Thr Cys Leu Val Lys Gly Phe Tyr Pro Ser Asp Ile Ala Val Glu
                580                 585                 590

Trp Glu Ser Asn Gly Gln Pro Glu Asn Asn Tyr Lys Thr Thr Pro Pro
                595                 600                 605

Val Leu Asp Ser Asp Gly Ser Phe Phe Leu Tyr Ser Lys Leu Thr Val
                610                 615                 620

Asp Lys Ser Arg Trp Gln Gln Gly Asn Val Phe Ser Cys Ser Val Met
625                 630                 635                 640

His Glu Ala Leu His Asn His Tyr Thr Gln Lys Ser Leu Ser Leu Ser
                645                 650                 655

Pro Gly Lys

<210> SEQ ID NO 17
<211> LENGTH: 1995
<212> TYPE: DNA
<213> ORGANISM: Artificial Sequence
<220> FEATURE:
<223> OTHER INFORMATION: laboratory-synthesized sequence

<400> SEQUENCE: 17
atgccgtctt ctgtctcgtg gggcatcctc ctgctggcag gcctgtgctg cctggtccct      60
gtctccctgg ctgaggatcc ccagggagat gctgcccaga gacagataca tcccaccat     120
gatcaggatc acccaacctt caacaagatc accccaaacc tggctgagtt cgccttcagc     180
ctataccgcc agctggcaca ccagtccaac agcaccaata tcttcttctc cccagtgagc     240
atcgctacag cctttgcaat gctctccctg gggaccaagg ctgacactca cgatgaaatc     300
ctggagggcc tgaatttcaa cctcacggag attccggagg ctcagatcca tgaaggcttc     360
caggaactcc tccgtaccct caaccagcca gacagccagc tccagctgac caccggcaat     420
ggcctgttcc tcagcgaggg cctgaagcta gtggataagt ttttggagga tgttaaaaag     480
ttgtaccact cagaagcctt cactgtcaac ttcggggaca ccgaagaggc caagaaacag     540
atcaacgatt acgtggagaa gggtactcaa gggaaaattg tggatttggt caaggagctt     600
gacagagaca cagttttgc tctggtgaat acatcttct ttaaaggcaa atgggagaga     660
ccctttgaag tcaaggacac cgaggaagag gacttccacg tggaccaggt gaccaccgtg     720
aaggtgccta tgatgaagcg tttaggcatg tttaacatcc agcactgtaa gaagctgtcc     780
agctgggtgc tgctgatgaa atacctgggc aatgccaccg ccatcttctt cctgcctgat     840
gaggggaaac tacagcacct ggaaaatgaa ctcacccacg atatcatcac caagttcctg     900
gaaaatgaag acagaaggtc tgccagctta catttaccca aactgtccat tactggaacc     960
tatgatctga gagcgtcct gggtcaactg gcatcacta aggtcttcag caatggggct    1020
gacctctccg ggtcacaga ggaggcaccc ctgaagctct ccaaggccgt gcataaggct    1080
gtgctgacca tcgacgagaa agggactgaa gctgctgggg ccatgttttt agaggccata    1140
cccatgtcta tccccccga ggtcaagttc aacaaaccct tgtcttctt aatgattgaa    1200
caaaatacca agtctcccct cttcatggga aagtggtga atcccacca aaaccatgg    1260
ggtggaggcg gttcaagagg tcctacgatc aagccctgcc cgcctagatc tgacaaaact    1320
```

-continued

```
cacacatgcc caccgtgccc agcacctgaa ctcgaggggg gaccgtcagt cttcctcttc    1380 ccccaaaac ccaaggacac cctcatgatc tcccggaccc ctgaggtcac atgcgtggtg     1440
gtggacgtga gccacgaaga ccctgaggtc aagttcaact ggtacgtgga cggcgtggag    1500
gtgcataatg ccaagacaaa gccgcgggag gagcagtaca acagcacgta ccgtgtggtc    1560
agcgtcctca ccgtcctgca ccaggactgg ctgaatggca aggcgtacaa ggccgcggtc    1620
tccaacaaag ccctcccagc ccccatcgag aaaaccatct ccaaagccaa agggcagccc    1680
cgagaaccac aggtgtacac cctgccccca tcccgggagg agatgaccaa gaaccaggtc    1740
agcctgacct gcctggtcaa aggcttctat cccagcgaca tcgccgtgga gtgggagagc    1800
aatgggcagc cggagaacaa ctacaagacc acgcctcccg tgctggactc cgacggctcc    1860
ttcttcctct acagcaagct caccgtggac aagagcaggt ggcagcaggg gaacgtcttc    1920
tcatgctccg tgatgcacga ggctctgcac aaccactaca cgcagaagag cctctccctg    1980
tctccgggta aataa                                                     1995
```

<210> SEQ ID NO 18
<211> LENGTH: 664
<212> TYPE: PRT
<213> ORGANISM: Artificial Sequence
<220> FEATURE:
<223> OTHER INFORMATION: laboratory-synthesized sequence

<400> SEQUENCE: 18

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
        50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240
```

```
Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys Pro Trp Gly Gly Gly Ser Arg Gly Pro Thr Ile Lys Pro
            420                 425                 430

Cys Pro Pro Arg Ser Asp Lys Thr His Thr Cys Pro Pro Cys Pro Ala
        435                 440                 445

Pro Glu Leu Glu Gly Gly Pro Ser Val Phe Leu Phe Pro Pro Lys Pro
    450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
        515                 520                 525

Asp Trp Leu Asn Gly Lys Ala Tyr Lys Ala Ala Val Ser Asn Lys Ala
    530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
                565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
        595                 600                 605

Lys Thr Thr Pro Pro Val Leu Asp Ser Asp Gly Ser Phe Phe Leu Tyr
    610                 615                 620

Ser Lys Leu Thr Val Asp Lys Ser Arg Trp Gln Gln Gly Asn Val Phe
625                 630                 635                 640
```

```
Ser Cys Ser Val Met His Glu Ala Leu His Asn His Tyr Thr Gln Lys
            645                 650                 655

Ser Leu Ser Leu Ser Pro Gly Lys
            660

<210> SEQ ID NO 19
<211> LENGTH: 38
<212> TYPE: DNA
<213> ORGANISM: Artificial Sequence
<220> FEATURE:
<223> OTHER INFORMATION: laboratory-synthesized sequence

<400> SEQUENCE: 19
ccttagatct atgccgtctt ctgtctcgtg gggcatcc                              38

<210> SEQ ID NO 20
<211> LENGTH: 41
<212> TYPE: DNA
<213> ORGANISM: Artificial Sequence
<220> FEATURE:
<223> OTHER INFORMATION: laboratory-synthesized sequence

<400> SEQUENCE: 20
ccttgctagc ttattttttgg gtgggattca ccacttttcc c                         41

<210> SEQ ID NO 21
<211> LENGTH: 38
<212> TYPE: DNA
<213> ORGANISM: Artificial Sequence
<220> FEATURE:
<223> OTHER INFORMATION: laboratory-synthesized sequence

<400> SEQUENCE: 21
ccttgaattc atgccgtctt ctgtctcgtg gggcatcc                              38

<210> SEQ ID NO 22
<211> LENGTH: 38
<212> TYPE: DNA
<213> ORGANISM: Artificial Sequence
<220> FEATURE:
<223> OTHER INFORMATION: laboratory-synthesized sequence

<400> SEQUENCE: 22
ccttccatgg tttttgggtg ggattcacca cttttccc                              38
```

α1-ANTITRYPSIN COMPOSITIONS AND METHODS OF TREATING AUTOIMMUNE DISEASES

CROSS-REFERENCE TO RELATED APPLICATIONS

This application is a continuation of U.S. patent application Ser. No. 15/317,136, filed Dec. 8, 2016, which is the U.S. National Phase Application under 35 U.S.C. § 371 of International Application No. PCT/US2015/035385, filed on Jun. 11, 2015, which claims the benefit of U.S. Application No. 62/010,741, filed on Jun. 11, 2014, which are incorporated by reference herein in their entireties.

TECHNICAL FIELD

The present invention relates generally to the treatment of autoimmune disease, e.g., diabetes, e.g., Type 1 and Type 2 diabetes. The treatment methods are varied and can include administration of an a1-antitrypsin polypeptide (AAT) conjugated to an Fc region of an immunoglobulin.

BACKGROUND

Diabetes is a very common disease that develops when the body does not produce enough, or appreciably any, insulin or cannot properly use or respond to insulin. There are two major types of diabetes. Type 1 diabetes is also known as insulin-dependent diabetes mellitus (IDDM) and results from insufficient insulin production. The onset of Type 1 diabetes is now known to occur in children, adolescents, or adults and is regarded as an autoimmune disease. Type 2 diabetes is known as noninsulin-dependent diabetes mellitus (NIDDM) and is the most common form of the disease, accounting for about 90% of all cases of diabetes. Typically, Type 2 diabetes, in the initial phases, is characterized by a suboptimal response to insulin. Although insulin is produced, the ability of a given amount of insulin needed to effect a given decrease in blood glucose is increased. In Type 2 diabetes, subjects manifest a blunted blood glucose response to insulin, i.e., a state of insulin resistance. The causes of diabetes are not completely understood, although both genetic and environmental factors, such as obesity and lack of exercise, increase the risk.

Type 1 diabetes is treated with insulin, although other treatments have been proposed and transplantation of the pancreas or insulin-producing islet cells from the pancreas has been used. Non-pharmaceutical intervention is usually prescribed initially for Type 2 diabetes, e.g., diet modification, weight loss, and exercise. If this is not successful, subjects are then generally treated with one of three different types of drugs: drugs that stimulate the release of insulin from the pancreas; drugs that increase a subject's sensitivity to insulin; and drugs that directly affect the circulating levels of glucose (e.g., drugs that decrease the production of glucose from the liver or increase its uptake by muscles). More specifically, a subject may be prescribed a sulfonylurea, an α-glucosidase inhibitor, metformin (GLUCOPHAGE™), or troglitazone (REZULIN™) In many cases, insulin is also used. After many years of living with Type 2 diabetes, some subjects manifest exhaustion of the insulin producing apparatus and thereby require insulin therapy. More recently, bariatric surgical procedures have been used with some success in those with extreme obesity and Type 2 diabetes. Despite the progress in understanding and treating diabetes, none of the current treatment strategies are optimal, and there is a great need for better ways to treat subjects who have diabetes or who are at risk of developing diabetes.

SUMMARY

The present invention is based, in part, on the discovery that a methionine-rich protein, e.g., AAT, can be purified without oxidizing its methionine residues. Further, the circulating half-life of AAT can be increased by conjugating it to an Fc region of an immunoglobulin and can be used in compositions and methods to treat autoimmune disease, e.g., diabetes, e.g., Type 1 and Type 2 diabetes. The present disclosure provides purified chimeric AAT-Fc polypeptides, e.g., recombinant polypeptides, comprising AAT conjugated to an Fc region of an immunoglobulin that are surprisingly more active, i.e., more strongly inhibit serine proteases, than wild type or commercial preparations of AAT. Accordingly, in one aspect, the present specification provides chimeric AAT-Fc polypeptides, e.g., recombinant polypeptides, comprising AAT conjugated to an Fc region of an immunoglobulin. For example, in one embodiment, AAT can comprise an amino acid sequence that is at least 90%, e.g., at least 92%, 95%, 96%, 97%, 98%, 99%, or 100% identical to SEQ ID NO:2. In one embodiment, the Fc region of the immunoglobulin can comprise an amino acid sequence that is at least 90%, e.g., at least 92%, 95%, 96%, 97%, 98%, 99%, or 100% identical to SEQ ID NO:4 or 6. In one embodiment, AAT conjugated to an Fc region of an immunoglobulin can comprise an amino acid sequence that is at least 90%, e.g., at least 92%, 95%, 96%, 97%, 98%, 99%, or 100% identical to SEQ ID NO: 8, 10, 12, 14, 16, or 18.

In another aspect, pharmaceutical compositions comprising a polypeptide comprising AAT conjugated to an Fc region of an immunoglobulin are provided with a pharmaceutically acceptable carrier.

In yet another aspect, nucleic acid molecules encoding a polypeptide comprising AAT conjugated to an Fc region of an immunoglobulin are described. For example, AAT can include an amino acid sequence that is at least 90%, e.g., at least 92%, 95%, 96%, 97%, 98%, 99%, or 100% identical to SEQ ID NO:2. In one embodiment, the nucleic acid sequence encoding AAT is at least 90%, e.g., at least 92%, 95%, 96%, 97%, 98%, 99%, or 100% identical to SEQ ID NO:1. In some embodiments, the Fc region of an immunoglobulin can comprise an amino acid sequence that is at least 90%, e.g., at least 92%, 95%, 96%, 97%, 98%, 99%, or 100% identical to SEQ ID NO:4 or 6. In one embodiment, the nucleic acid sequence encoding the Fc region of the immunoglobulin is at least 90%, e.g., at least 92%, 95%, 96%, 97%, 98%, 99%, or 100% identical to SEQ ID NO:3 or 5. In some instances, AAT conjugated to an Fc region of an immunoglobulin comprises an amino acid sequence that is at least 90%, e.g., at least 92%, 95%, 96%, 97%, 98%, 99%, or 100% identical to SEQ ID NO:8, 10, 12, 14, 16, or 18, or a nucleic acid sequence that is at least 90%, e.g., at least 92%, 95%, 96%, 97%, 98%, 99%, or 100% identical to SEQ ID NO:7, 9, 11, 13, 15, or 17.

In still another aspect, vectors comprising a nucleic acid molecule encoding a polypeptide comprising AAT conjugated to an Fc region of an immunoglobulin, are described. Pharmaceutical compositions comprising the vector are also provided. The vector can also be comprised within a cell, e.g., bacterial cell, insect cell, mammalian, e.g., human, cell.

In a further aspect, methods of purifying and isolating methionine-rich proteins, e.g., AAT conjugated or not conjugated to an Fc region of an immunoglobulin or linked with other protein(s), are described. The methods can include providing a cell comprising a nucleic acid molecule encoding a polypeptide comprising AAT or AAT conjugated to an Fc region of an immunoglobulin or linked with other protein(s); and culturing the cell under conditions sufficient to produce AAT or AAT conjugated to an Fc region of an immunoglobulin or linked with other protein(s), e.g., in growth media with at least 10 mM, e.g., at least 20 mM, 50 mM, 100 mM, 200 mM, or 500 mM, methionine, thereby producing AAT or AAT conjugated to an Fc region of an immunoglobulin or linked with other protein(s). The methods include purifying or isolating AAT or AAT conjugated to an Fc region of an immunoglobulin or linked with other protein(s) from the cell by including at least 10 mM, e.g., at least 20 mM, 50 mM, 100 mM, 200 mM, or 500 mM, methionine in standard purification reagents and/or isolation reagents, e.g., extraction buffers, wash buffers, and/or elution buffers, supplemented with methionine.

In yet another aspect, methods of treating autoimmune disease, e.g., diabetes, e.g., Type 1 and Type 2 diabetes, in a subject, e.g., a mammal, a human, are described. The methods comprise administering, e.g., subcutaneously, intraperitoneally, intramuscularly, orally, or by infusion, to a subject a therapeutically effective amount of AAT that is conjugated to an Fc region of an immunoglobulin, to thereby treat autoimmune disease, e.g., diabetes, e.g., Type 1 and Type 2 diabetes, in the subject. The methods can further include treating the subject with insulin. Also within the invention is the use of AAT conjugated to an Fc region of an immunoglobulin, as described herein, to manufacture a medicament to treat autoimmune disease, e.g., diabetes, e.g., Type 1 and Type 2 diabetes.

In one embodiment, the methods further comprise selecting the subject, wherein selecting the subject comprises providing a sample, e.g., serum, plasma, or blood, from the subject; assaying the sample to determine a level of glucose in the sample to obtain a test value; comparing the test value to a reference value; and selecting the subject (e.g., selecting the subject for treatment) if the test value is greater than or in certain instances about the same as the reference value.

As used herein, "treatment" or "treating" is an approach for obtaining beneficial or desired results, including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing, reducing risk, or preventing or delaying the recurrence of the disease following a pancreas or islet cell transplant, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of autoimmune disease. The methods of the invention contemplate any one or more of these aspects of treatment.

Unless otherwise defined, all technical terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control. Other features and advantages of the invention will be apparent from the following detailed description and figures, and from the claims.

DESCRIPTION OF DRAWINGS

FIG. 1 is a schematic diagram showing human AAT fused to a Fc region of a human IgG.

DETAILED DESCRIPTION

Figure 2:
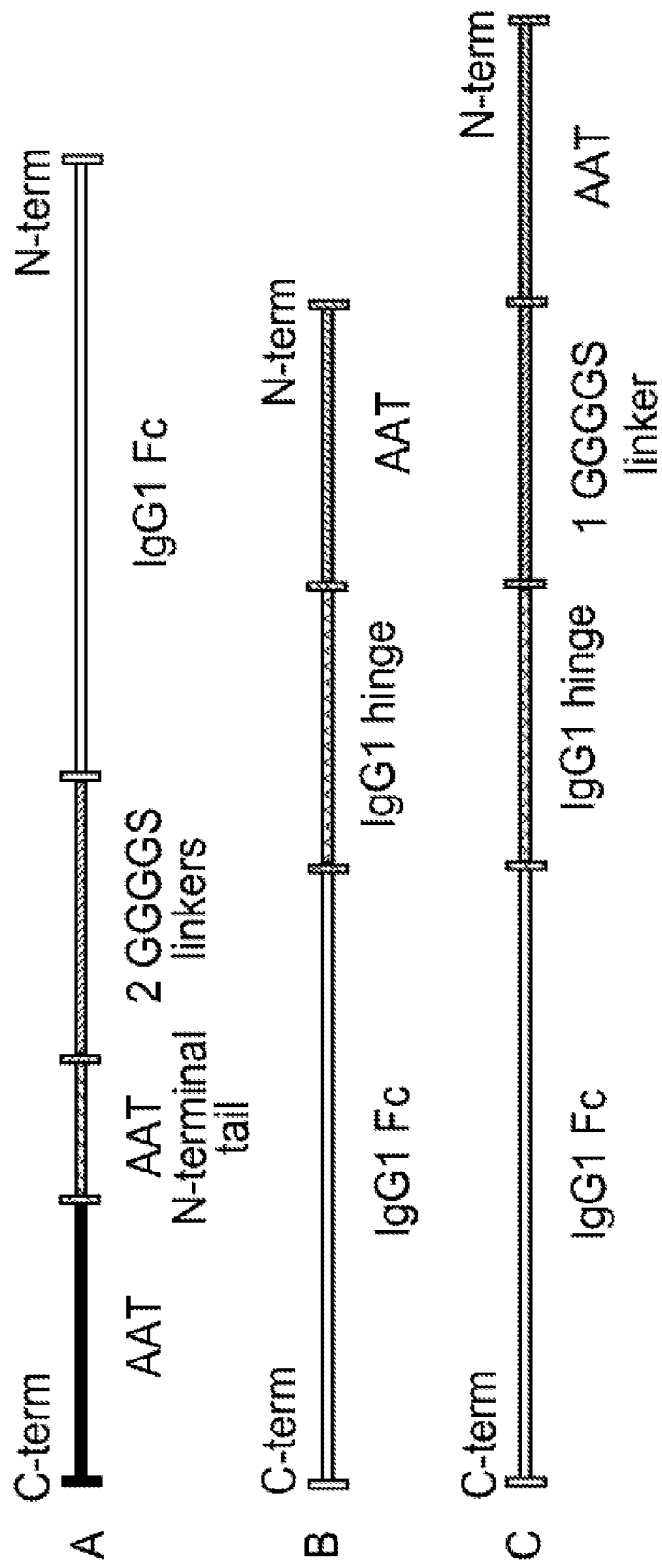
FIG. 2 is a schematic diagram showing three different AAT-Fc constructs, with FIG. 2A representing Construct 1 (SEQ ID NO:8) and Construct 4 (SEQ ID NO:14), FIG. 2B representing Construct 2 (SEQ ID NO:10) and Construct 5 (SEQ ID NO:16), and FIG. 2C representing Construct 3 (SEQ ID NO:12 and Construct 6 (SEQ ID NO:18).

AAT is a serpin that acts as an inhibitor of various serine proteases, but its primary target is elastase. In the absence of AAT, elastase is free to break down elastin, which leads to loss of elasticity of the lungs and results in respiratory complications such as emphysema and chronic obstructive pulmonary disease (COPD). AAT irreversibly inhibits trypsin, chymotrypsin, and plasminogen activator. An aberrant form inhibits insulin-induced nitric oxide synthesis in platelets, decreases coagulation time, and has proteolytic activity against insulin and plasmin (Tanaka et al., *Jpn J Cancer Res* 82:693-700, 1991; and Niemann et al., *Matrix* 12:233-41, 1992).

AAT restores normoglycemia in new onset diabetic non-obese diabetic (NOD) mice, a daunting and clinically predictive model for Type 1 diabetes (Koulmanda et al., *Proc Natl Acad Sci USA* 105:16242-7, 2008). Many agents have proven effective in preventing frank diabetes when given after early signs of autoimmunity are present, but very few of these agents are effective after the onset of hyperglycemia. Some, but not many, of these agents work after establishment of significant islet cell damage in advance of elevated blood glucose levels.

AAT is commercially available from Baxter International Inc., which markets AAT as ARALAST™ for the treatment of chronic augmentation therapy in patients with hereditary emphysema. ARALAST™ is prepared from large pools of human plasma by using the Cohn-Oncley cold alcohol fractionation process, followed by purification steps including polyethylene glycol and zinc chloride precipitation and ion exchange chromatography. ARALAST™ contains AAT with a truncated C-terminal lysine, whereby the Lys394 residue has been removed. Because the metabolic half-life of ARALAST™ is only about 5.9 days, dosing is required approximately once weekly (e.g., with a dosage of 60 mg/kg body weight). Further, since commercial AAT is derived from pooled human plasma, it may carry a risk of transmitting infectious agents, e.g., viruses and theoretically, the Creutzfeldt-Jakob disease (CJD) agent. Such products can therefore transmit disease. ARALAST™ may also contain trace amounts of IgA. Patients with known antibodies against IgA, which can be present in patients with selective or severe IgA deficiency, have a greater risk of developing potentially severe hypersensitivity and anaphylactic reactions. ARALAST™ is contraindicated in patients with antibodies against IgA due to risk of severe hypersensitivity.

The present disclosure provides purified, chimeric, recombinant AAT polypeptides that are more active and have longer in vivo circulating half-lives than commercial AAT. For example, heterologous polypeptides of AAT conjugated to an Fc region of an immunoglobulin (e.g., a subclass of antibodies that lacks the heavy chain variable region) are described. AAT can be conjugated to an Fc region of an immunoglobulin molecule of any class (e.g., IgG, IgM, IgA, IgD, and IgE). Described herein is a chimeric, recombinant fusion protein consisting of two AATs conjugated to an Fc region of a human IgG1 molecule and methods of making and using such proteins. Skilled practitioners will appreciate that the chimeric AAT-Fc polypeptides and methods may be modified to involve a variant or an active fragment of AAT and an Fc region of an immunoglobulin molecule of isotype IgG1, IgG2, IgG3, IgG4, IgA1, IgA2, IgD, IgE, or IgM. For example, AAT can include a full-length, soluble form of the enzyme, or a portion or other mutant thereof that retains sufficient activity to reduce activity of the target of interest to a clinically useful extent, e.g., elastase. AAT can be conjugated to an Fc region of an immunoglobulin molecule at the N-terminal or C-terminal end of AAT. Further, the Fc region may include a mutation that inhibits complement fixation and Fc receptor binding, or it may be lytic (i.e., able to bind complement or to lyse cells via another mechanism, such as antibody-dependent complement lysis (ADCC)).

Nucleic Acids, Proteins, Vectors, and Host Cells

Figure 1:
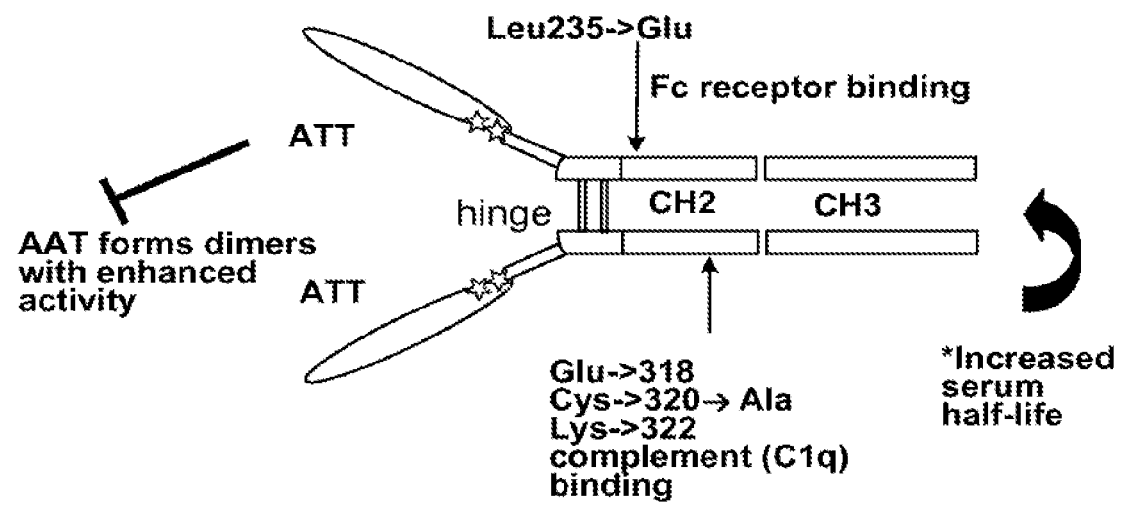

In one aspect, AAT can be conjugated or fused to an Fc region of an immunoglobulin, e.g., IgG1. AAT can be conjugated directly to an Fc region of an immunoglobulin or indirectly through use of a short peptide linker, usually less than 20 amino acids in length, e.g., five amino acids, e.g., GGGGS, or 10 amino acids, e.g., GGGGSGGGGS. Also within the invention are nucleic acids that encode an AAT conjugated or fused to an Fc region of an immunoglobulin. As shown in FIG. 1, AAT can be conjugated to an Fc region of an IgG, in which case two AAT polypeptides (or therapeutically active variants thereof) are included in a single molecule.

AAT is synthesized in the liver and secreted into the plasma, where it is abundant at levels of approximately 1.5 to 3.5 mg/ml of blood. The human AAT sequence is known in the art; exemplary reference sequences can be found in the GenBank database at accession number NM 000295.4 (nucleic acid) and NP 000286.3 (amino acid). See also GeneID: 5265. AAT is encoded by a 1157 base pair sequence found on chromosome 14 of the human genome (SEQ ID NO:1). The pro-peptide, as shown below, is 418 residues long (SEQ ID NO:2). In mature form, AAT is a single glycoprotein consisting of 394 amino acids with a molecular weight of 46,737 and an isoelectric point of 5.37. Further analysis reveals three potential sites to be N-glycosylated and these three asparagine residues (N) are located at N70, N107, and N271.

Human AAT Nucleic Acid Sequence

```
                                                          (SEQ ID NO: 1)
   1    ATGCCGTCTT CTGTCTCGTG GGGCATCCTC CTGCTGGCAG GCCTGTGCTG CCTGGTCCCT

61    GTCTCCCTGG CTGAGGATCC CCAGGGAGAT GCTGCCCAGA AGACAGATAC ATCCCACCAT

121    GATCAGGATC ACCCAACCTT CAACAAGATC ACCCCCAACC TGGCTGAGTT CGCCTTCAGC

181    CTATACCGCC AGCTGGCACA CCAGTCCAAC AGCACCAATA TCTTCTTCTC CCCAGTGAGC

241    ATCGCTACAG CCTTTGCAAT GCTCTCCCTG GGGACCAAGG CTGACACTCA CGATGAAATC

301    CTGGAGGGCC TGAATTTCAA CCTCACGGAG ATTCCGGAGG CTCAGATCCA TGAAGGCTTC

361    CAGGAACTCC TCCGTACCCT CAACCAGCCA GACAGCCAGC TCCAGCTGAC CACCGGCAAT

421    GGCCTGTTCC TCAGCGAGGG CCTGAAGCTA GTGGATAAGT TTTTGGAGGA TGTTAAAAAG

481    TTGTACCACT CAGAAGCCTT CACTGTCAAC TTCGGGGACA CCGAAGAGGC CAAGAAACAG

541    ATCAACGATT ACGTGGAGAA GGGTACTCAA GGGAAAATTG TGGATTTGGT CAAGGAGCTT

601    GACAGAGACA CAGTTTTTGC TCTGGTGAAT TACATCTTCT TTAAAGGCAA ATGGGAGAGA

661    CCCTTTGAAG TCAAGGACAC CGAGGAAGAG GACTTCCACG TGGACCAGGT GACCACCGTG

721    AAGGTGCCTA TGATGAAGCG TTTAGGCATG TTTAACATCC AGCACTGTAA GAAGCTGTCC

781    AGCTGGGTGC TGCTGATGAA ATACCTGGGC AATGCCACCG CCATCTTCTT CCTGCCTGAT

841    GAGGGGAAAC TACAGCACCT GGAAAATGAA CTCACCCACG ATATCATCAC CAAGTTCCTG

901    GAAAATGAAG ACAGAAGGTC TGCCAGCTTA CATTTACCCA AACTGTCCAT TACTGGAACC

961    TATGATCTGA AGAGCGTCCT GGGTCAACTG GGCATCACTA AGGTCTTCAG CAATGGGGCT

1021    GACCTCTCCG GGGTCACAGA GGAGGCACCC CTGAAGCTCT CCAAGGCCGT GCATAAGGCT

1081    GTGCTGACCA TCGACGAGAA AGGGACTGAA GCTGCTGGGG CCATGTTTTT AGAGGCCATA
```

```
1041  CCCATGTCTA TCCCCCCCGA GGTCAAGTTC AACAAACCCT TTGTCTTCTT AATGATTGAA

1101  CAAAATACCA AGTCTCCCCT CTTCATGGGA AAAGTGGTGA ATCCCACCCA AAAATAA
```

Human AAT Protein Sequence

```
                                                                  (SEQ ID NO: 2)
  1  MPSSVSWGIL LLAGLCCLVP VSLAEDPQGD AAQKTDTSHH DQDHPTFNKI TPNLAEFAFS

61  LYRQLAHQSN STNIFFSPVS IATAFAMLSL GTKADTHDEI LEGLNFNLTE IPEAQIHEGF

121  QELLRTLNQP DSQLQLTTGN GLFLSEGLKL VDKFLEDVKK LYHSEAFTVN FGDTEEAKKQ

181  INDYVEKGTQ GKIVDLVKEL DRDTVFALVN YIFFKGKWER PFEVKDTEEE DFHVDQVTTV

241  KVPMMKRLGM FNIQHCKKLS SWVLLMKYLG NATAIFFLPD EGKLQHLENE LTHDIITKFL

301  ENEDRRSASL HLPKLSITGT YDLKSVLGQL GITKVFSNGA DLSGVTEEAP LKLSKAVHKA

361  VLTIDEKGTE AAGAMFLEAI PMSIPPEVKF NKPFVFLMIE QNTKSPLFMG KVVNPTQK
```

Six other examples of AAT are highlighted below in Table 1, and substantially identical nucleotide and protein sequences can also be used.

TABLE 1

AAT orthologs from seven different species along with their GenBank RefSeq Accession Numbers.

| Species | Nucleic Acid | Amino Acid | GeneID |
|---|---|---|---|
| Homo sapiens | NM_000295.4 | NP_000286.3 | 5265 |
| Mus musculus | NM_009245.2 | NP_033271.1 | 20702 |
| Rattus norvegicus | NM_022519.2 | NP_071964.2 | 24648 |
| Gallus gallus | XM_421344.2 | XP_421344.1 | 423435 |
| Pan troglodytes | XM_003314496.2 | XP_003314544.1 | 467451 |
| Canis familiaris | NM_001080109.1 | NP_001073578.1 | 480422 |
| Bos Taurus | NM_173882.1 | NP_776307.1 | 280699 |

In one aspect, the invention features nucleic acids encoding AAT-Fc fusion polypeptides, fragments, and variants thereof. A nucleic acid sequence encoding an exemplary AAT is provided as SEQ ID NO:1. The amino acid sequence encoded by SEQ ID NO:1 is provided as SEQ ID NO:2. A nucleic acid sequence encoding an exemplary Fc region of an IgG1 is provided as SEQ ID NO:3. The amino acid sequence encoded by SEQ ID NO:3 is provided as SEQ ID NO:4.

Human Fc Region of an IgG1 Nucleic Acid Sequence

```
                                                                  (SEQ ID NO: 3)
  1  GACAAAACTC ACACATGCCC ACCGTGCCCA GCACCTGAAC TCCTGGGGGG ACCGTCAGTC

61  TTCCTCTTCC CCCCAAAACC CAAGGACACC CTCATGATCT CCCGGACCCC TGAGGTCACA

121  TGCGTGGTGG TGGACGTGAG CCACGAAGAC CCTGAGGTCA AGTTCAACTG GTACGTGGAC

181  GGCGTGGAGG TGCATAATGC CAAGACAAAG CCGCGGGAGG AGCAGTACAA CAGCACGTAC

241  CGTGTGGTCA GCGTCCTCAC CGTCCTGCAC CAGGACTGGC TGAATGGCAA GGAGTACAAG

301  TGCAAGGTCT CCAACAAAGC CCTCCCAGCC CCCATCGAGA AAACCATCTC CAAAGCCAAA

361  GGGCAGCCCC GAGAACCACA GGTGTACACC CTGCCCCCAT CCCGGGAGGA GATGACCAAG

421  AACCAGGTCA GCCTGACCTG CCTGGTCAAA GGCTTCTATC CAGCGACAT CGCCGTGGAG

481  TGGGAGAGCA ATGGGCAGCC GGAGAACAAC TACAAGACCA CGCCTCCCGT GCTGGACTCC

541  GACGGCTCCT TCTTCCTCTA CAGCAAGCTC ACCGTGGACA AGAGCAGGTG GCAGCAGGGG

601  AACGTCTTCT CATGCTCCGT GATGCACGAG GCTCTGCACA ACCACTACAC GCAGAAGAGC

661  CTCTCCCTGT CTCCGGGTAA A
```

Human Fc Region of an IgG1 Amino Acid Sequence

```
                                                          (SEQ ID NO: 4)
  1  DKTHTCPPCP APELLGGPSV FLFPPKPKDT LMISRTPEVT CVVVDVSHED PEVKFNWYVD

61  GVEVHNAKTK PREEQYNSTY RVVSVLTVLH QDWLNGKEYK CKVSNKALPA PIEKTISKAK

121  GQPREPQVYT LPPSREEMTK NQVSLTCLVK GFYPSDIAVE WESNGQPENN YKTTPPVLDS

181  DGSFFLYSKL TVDKSRWQQG NVFSCSVMHE ALHNHYTQKS LSLSPGK
```

In some embodiments, the Fc region of an immunoglobulin is mutated to render it non-lytic. For example, four residues were mutated in the Fc region of a human IgG1: Leu-15-Glu; Glu-98-Ala; Cys-101-Ala; and Lys-102-Ala, as shown below as SEQ ID NO:6, and the non-lytic human IgG1 is conjugated to an AAT polypeptide.

```
                                                          (SEQ ID NO: 5)
  1  GACAAAACTC ACACATGCCC ACCGTGCCCA GCACCTGAAC TCGAGGGGGG ACCGTCAGTC

61  TTCCTCTTCC CCCCAAAACC CAAGGACACC CTCATGATCT CCCGGACCCC TGAGGTCACA

121  TGCGTGGTGG TGGACGTGAG CCACGAAGAC CCTGAGGTCA AGTTCAACTG GTACGTGGAC

181  GGCGTGGAGG TGCATAATGC CAAGACAAAG CCGCGGGAGG AGCAGTACAA CAGCACGTAC

241  CGTGTGGTCA GCGTCCTCAC CGTCCTGCAC CAGGACTGGC TGAATGGCAA GGCGTACAAG

301  GCCGCGGTCT CCAACAAAGC CCTCCCAGCC CCCATCGAGA AAACCATCTC CAAAGCCAAA

361  GGGCAGCCCC GAGAACCACA GGTGTACACC CTGCCCCCAT CCCGGGAGGA GATGACCAAG

421  AACCAGGTCA GCCTGACCTG CCTGGTCAAA GGCTTCTATC CCAGCGACAT CGCCGTGGAG

481  TGGGAGAGCA ATGGGCAGCC GGAGAACAAC TACAAGACCA CGCCTCCCGT GCTGGACTCC

541  GACGGCTCCT TCTTCCTCTA CAGCAAGCTC ACCGTGGACA AGAGCAGGTG GCAGCAGGGG

601  AACGTCTTCT CATGCTCCGT GATGCACGAG GCTCTGCACA ACCACTACAC GCAGAAGAGC

661  CTCTCCCTGT CTCCGGGTAA A
```

```
                                                          (SEQ ID NO: 6)
  1  DKTHTCPPCP APELEGGPSV FLFPPKPKDT LMISRTPEVT CVVVDVSHED PEVKFNWYVD

61  GVEVHNAKTK PREEQYNSTY RVVSVLTVLH QDWLNGKAYK AAVSNKALPA PIEKTISKAK

121  GQPREPQVYT LPPSREEMTK NQVSLTCLVK GFYPSDITVE WESNGQPENN YKTTPPVLDS

181  DGSFFLYSKL TVDKSRWQQG NVFSCSVMHE ALHNHYTQKS LSLSPGK
```

In one embodiment, an AAT polypeptide is conjugated to an Fc region of IgG1 at the N-terminus of AAT with two GGGGS linkers ("Construct 1") (FIG. 2A). A nucleic acid sequence encoding an AAT polypeptide conjugated to an Fc region of IgG1 at the N-terminus of AAT with two GGGGS linkers is provided as SEQ ID NO:7. The amino acid sequence encoded by SEQ ID NO:7 is provided as SEQ ID NO:8, which comprises an IL2 signal peptide sequence, the sequence of an Fc region of IgG1, two GGGGS linkers, and the sequence of an AAT polypeptide.

```
                                                          (SEQ ID NO: 7)
  1  ATGTACAGGA TGCAACTCCT GTCTTGCATT GCACTAAGTC TTGCACTTGT CACGAATTCG

61  GATATCGACA AAACTCACAC ATGCCCACCG TGCCCAGCAC CTGAACTCCT GGGGGGACCG

121  TCAGTCTTCC TCTTCCCCCC AAAACCCAAG GACACCCTCA TGATCTCCCG GACCCCTGAG

181  GTCACATGCG TGGTGGTGGA CGTGAGCCAC GAAGACCCTG AGGTCAAGTT CAACTGGTAC

241  GTGGACGGCG TGGAGGTGCA TAATGCCAAG ACAAAGCCGC GGGAGGAGCA GTACAACAGC

301  ACGTACCGTG TGGTCAGCGT CCTCACCGTC CTGCACCAGG ACTGGCTGAA TGGCAAGGAG

361  TACAAGTGCA AGGTCTCCAA CAAAGCCCTC CCAGCCCCCA TCGAGAAAAC CATCTCCAAA
```

-continued

```
 421  GCCAAAGGGC AGCCCCGAGA ACCACAGGTG TACACCCTGC CCCCATCCCG GGAGGAGATG
 481  ACCAAGAACC AGGTCAGCCT GACCTGCCTG GTCAAAGGCT TCTATCCCAG CGACATCGCC
 541  GTGGAGTGGG AGAGCAATGG GCAGCCGGAG AACAACTACA AGACCACGCC TCCCGTGCTG
 601  GACTCCGACG GCTCCTTCTT CCTCTACAGC AAGCTCACCG TGGACAAGAG CAGGTGGCAG
 661  CAGGGGAACG TCTTCTCATG CTCCGTGATG CACGAGGCTC TGCACAACCA CTACACGCAG
 721  AAGAGCCTCT CCCTGTCTCC GGGTAAACCA TGGGGTGGAG CGGTTCAGG CGGAGGTGGC
 781  TCTAGATCTG CTGCCCAGAA GACAGATACA TCCCACCATG ATCAGGATCA CCCAACCTTC
 841  AACAAGATCA CCCCCAACCT GGCTGAGTTC GCCTTCAGCC TATACCGCCA GCTGGCACAC
 901  CAGTCCAACA GCACCAATAT CTTCTTCTCC CCAGTGAGCA TCGCTACAGC CTTTGCAATG
 961  CTCTCCCTGG GGACCAAGGC TGACACTCAC GATGAAATCC TGGAGGGCCT GAATTTCAAC
1021  CTCACGGAGA TTCCGGAGGC TCAGATCCAT GAAGGCTTCC AGGAACTCCT CCGTACCCTC
1081  AACCAGCCAG ACAGCCAGCT CCAGCTGACC ACCGGCAATG GCCTGTTCCT CAGCGAGGGC
1141  CTGAAGCTAG TGGATAAGTT TTTGGAGGAT GTTAAAAAGT TGTACCACTC AGAAGCCTTC
1201  ACTGTCAACT TCGGGGACAC CGAAGAGGCC AAGAAACAGA TCAACGATTA CGTGGAGAAG
1261  GGTACTCAAG GGAAAATTGT GGATTTGGTC AAGGAGCTTG ACAGAGACAC AGTTTTTGCT
1321  CTGGTGAATT ACATCTTCTT TAAAGGCAAA TGGGAGAGAC CCTTTGAAGT CAAGGACACC
1381  GAGGAAGAGG ACTTCCACGT GGACCAGGTG ACCACCGTGA AGGTGCCTAT GATGAAGCGT
1441  TTAGGCATGT TTAACATCCA GCACTGTAAG AAGCTGTCCA GCTGGGTGCT GCTGATGAAA
1501  TACCTGGGCA ATGCCACCGC CATCTTCTTC CTGCCTGATG AGGGGAAACT ACAGCACCTG
1561  GAAAATGAAC TCACCCACGA TATCATCACC AAGTTCCTGG AAAATGAAGA CAGAAGGTCT
1621  GCCAGCTTAC ATTTACCCAA ACTGTCCATT ACTGGAACCT ATGATCTGAA GAGCGTCCTG
1681  GGTCAACTGG GCATCACTAA GGTCTTCAGC AATGGGGCTG ACCTCTCCGG GGTCACAGAG
1741  GAGGCACCCC TGAAGCTCTC CAAGGCCGTG CATAAGGCTG TGCTGACCAT CGACGAGAAA
1801  GGGACTGAAG CTGCTGGGGC CATGTTTTTA GAGGCCATAC CCATGTCTAT CCCCCCCGAG
1861  GTCAAGTTCA ACAAACCCTT TGTCTTCTTA ATGATTGAAC AAAATACCAA GTCTCCCCTC
1921  TTCATGGGAA AAGTGGTGAA TCCCACCCAA AAATAA
```

(SEQ ID NO: 8)
```
  1  MYRMQLLSCI ALSLALVTNS DIDKTHTCPP CPAPELLGGP SVFLFPPKPK DTLMISRTPE
 61  VTCVVVDVSH EDPEVKFNWY VDGVEVHNAK TKPREEQYNS TYRVVSVLTV LHQDWLNGKE
121  YKCKVSNKAL RAPIEKTISK AKGQPREPQV YTLPPSREEM TKNQVSLTCL VKGFYPSDIA
181  VEWESNGQPE NNYKTTPPVL DSDGSFFLYS KLTVDKSRWQ QGNVFSCSVM HEALHNHYTQ
241  KSLSLSPGKP WGGGSGGGG SRSAAQKTDT SHHDQDHPTF NKITPNLAEF AFSLYRQLAH
301  QSNSTNIFFS PVSIATAFAM LSLGTKADTH DEILEGLNFN LTEIPEAQIH EGFQELLRTL
361  NQPDSQLQLT TGNGLFLSEG LKLVDKFLED VKKLYHSEAF TVNFGDTEEA KKQINDYVEK
421  GTQGKIVDLV KELDRDTVFA LVNYIFFKGK WERPFEVKDT EEEDFHVDQV TTVKVPMMKR
481  LGMFNIQHCK KLSSWVLLMK YLGNATAIFF LPDEGKLQHL ENELTHDIIT KFLENEDRRS
```

```
541    ASLHLPKLSI TGTYDLKSVL GQLGITKVFS NGADLSGVTE EAPLKLSKAV HKAVLTIDEK

601    GTEAAGAMFL EAIPMSIPPE VKFNKPFVFL MIEQNTKSPL FMGKVVNPTQ K
```

In one embodiment, the AAT polypeptide is directly conjugated to an Fc region of IgG1 at the C-terminus of AAT ("Construct 2") (FIG. 2B). A nucleic acid sequence encoding an AAT polypeptide directly conjugated to an Fc region of IgG1 at the C terminus of AAT is provided as SEQ ID NO:9. The amino acid sequence encoded by SEQ ID NO:9 is provided as SEQ ID NO:10, which comprises the sequence of an AAT polypeptide, an IgG1 hinge sequence, and the sequence of an Fc region of IgG1.

```
                                                                     (SEQ ID NO: 9)
   1    ATGCCGTCTT CTGTCTCGTG GGGCATCCTC CTGCTGGCAG GCCTGTGCTG CCTGGTCCCT

61    GTCTCCCTGG CTGAGGATCC CCAGGGAGAT GCTGCCCAGA AGACAGATAC ATCCCACCAT

121    GATCAGGATC ACCCAACCTT CAACAAGATC ACCCCCAACC TGGCTGAGTT CGCCTTCAGC

181    CTATACCGCC AGCTGGCACA CCAGTCCAAC AGCACCAATA TCTTCTTCTC CCCAGTGAGC

241    ATCGCTACAG CCTTTGCAAT GCTCTCCCTG GGGACCAAGG CTGACACTCA CGATGAAATC

301    CTGGAGGGCC TGAATTTCAA CCTCACGGAG ATTCCGGAGG CTCAGATCCA TGAAGGCTTC

361    CAGGAACTCC TCCGTACCCT CAACCAGCCA GACAGCCAGC TCCAGCTGAC CACCGGCAAT

421    GGCCTGTTCC TCAGCGAGGG CCTGAAGCTA GTGGATAAGT TTTTGGAGGA TGTTAAAAAG

481    TTGTACCACT CAGAAGCCTT CACTGTCAAC TTCGGGGACA CCGAAGAGGC CAAGAAACAG

541    ATCAACGATT ACGTGGAGAA GGGTACTCAA GGGAAAATTG TGGATTTGGT CAAGGAGCTT

601    GACAGAGACA CAGTTTTTGC TCTGGTGAAT TACATCTTCT TTAAAGGCAA ATGGGAGAGA

661    CCCTTTGAAG TCAAGGACAC CGAGGAAGAG GACTTCCACG TGGACCAGGT GACCACCGTG

721    AAGGTGCCTA TGATGAAGCG TTTAGGCATG TTTAACATCC AGCACTGTAA GAAGCTGTCC

781    AGCTGGGTGC TGCTGATGAA ATACCTGGGC AATGCCACCG CCATCTTCTT CCTGCCTGAT

841    GAGGGGAAAC TACAGCACCT GGAAAATGAA CTCACCCACG ATATCATCAC CAAGTTCCTG

901    GAAAATGAAG ACAGAAGGTC TGCCAGCTTA CATTTACCCA AACTGTCCAT TACTGGAACC

961    TATGATCTGA AGAGCGTCCT GGGTCAACTG GGCATCACTA AGGTCTTCAG CAATGGGGCT

1021    GACCTCTCCG GGGTCACAGA GGAGGCACCC CTGAAGCTCT CCAAGGCCGT GCATAAGGCT

1081    GTGCTGACCA TCGACGAGAA AGGGACTGAA GCTGCTGGGG CCATGTTTTT AGAGGCCATA

1141    CCCATGTCTA TCCCCCCCGA GGTCAAGTTC AACAAACCCT TTGTCTTCTT AATGATTGAA

1201    CAAAATACCA AGTCTCCCCT CTTCATGGGA AAGTGGTGA ATCCCACCCA AAAACCATGG

1261    AGAGGTCCTA CGATCAAGCC CTGCCCGCCT AGATCTGACA AAACTCACAC ATGCCCACCG

1321    TGCCCAGCAC CTGAACTCCT GGGGGGACCG TCAGTCTTCC TCTTCCCCCC AAAACCCAAG

1381    GACACCCTCA TGATCTCCCG GACCCCTGAG GTCACATGCG TGGTGGTGGA CGTGAGCCAC

1441    GAAGACCCTG AGGTCAAGTT CAACTGGTAC GTGGACGGCG TGGAGGTGCA TAATGCCAAG

1501    ACAAAGCCGC GGGAGGAGCA GTACAACAGC ACGTACCGTG TGGTCAGCGT CCTCACCGTC

1561    CTGCACCAGG ACTGGCTGAA TGGCAAGGAG TACAAGTGCA AGGTCTCCAA CAAAGCCCTC
```

-continued

```
1621  CCAGCCCCCA TCGAGAAAAC CATCTCCAAA GCCAAAGGGC AGCCCCGAGA ACCACAGGTG
1681  TACACCCTGC CCCCATCCCG GGAGGAGATG ACCAAGAACC AGGTCAGCCT GACCTGCCTG
1741  GTCAAAGGCT TCTATCCCAG CGACATCGCC GTGGAGTGGG AGAGCAATGG GCAGCCGGAG
1801  AACAACTACA AGACCACGCC TCCCGTGCTG GACTCCGACG GCTCCTTCTT CCTCTACAGC
1861  AAGCTCACCG TGGACAAGAG CAGGTGGCAG CAGGGGAACG TCTTCTCATG CTCCGTGATG
1921  CACGAGGCTC TGCACAACCA CTACACGCAG AAGAGCCTCT CCCTGTCTCC GGGTAAATAA
```

(SEQ ID NO: 10)
```
  1  MPSSVSWGIL LLAGLCCLVP VSLAEDPQGD AAQKTDTSHH DQDHPTFNKI TPNLAEFAFS
 61  LYRQLAHQSN STNIFFSPVS IATAFAMLSL GTKADTHDEI LEGLNFNLTE IPEAQIHEGF
121  QELLRTLNQP DSQLQLTTGN GLFLSEGLKL VDKFLEDVKK LYHSEAFTVN FGDTEEAKKQ
181  INDYVEKGTQ GKIVDLVKEL DRDTVFALVN YIFFKGKWER PFEVKDTEEE DFHVDQVTTV
241  KVPMMKRLGM FNIQHCKKLS SWVLLMKYLG NATAIFFLPD EGKLQHLENE LTHDIITKFL
301  ENEDRRSASL HLPKLSITGT YDLKSVLGQL GITKVFSNGA DLSGVTEEAP LKLSKAVHKA
361  VLTIDEKGTE AAGAMFLEAI PMSIPPEVKF NKPFVFLMIE QNTKSPLFMG KVVNPTQKPW
421  RGPTIKPCPP RSDKTHTCPP CPAPELLGGP SVFLFPPKPK DTLMISRTPE VTCVVVDVSH
481  EDPEVKFNWY VDGVEVHNAK TKPREEQYNS TYRVVSVLTV LHQDWLNGKE YKCKVSNKAL
541  PAPIEKTISK AKGQPREPQV YTLPPSREEM TKNQVSLTCL VKGFYPSDIA VEWESNGQPE
601  NNYKTTPPVL DSDGSFFLYS KLTVDKSRWQ QGNVFSCSVM HEALHNHYTQ KSLSLSPGK
```

In one embodiment, the AAT polypeptide is conjugated to an Fc region of IgG1 at the C-terminus of AAT with one GGGGS linker ("Construct 3") (FIG. 2C). A nucleic acid sequence encoding an exemplary AAT polypeptide conjugated to an Fc region of IgG1 at the C-terminus of AAT with one GGGGS linker is provided as SEQ ID NO:11. The amino acid sequence encoded by SEQ ID NO:11 is provided as SEQ ID NO:12, which comprises the sequence of an AAT polypeptide, a GGGGS linker, an IgG1 hinge sequence, and the sequence of an Fc region of IgG1.

(SEQ ID NO: 11)
```
   1  ATGCCGTCTT CTGTCTCGTG GGGCATCCTC CTGCTGGCAG GCCTGTGCTG CCTGGTCCCT
  61  GTCTCCCTGG CTGAGGATCC CCAGGGAGAT GCTGCCCAGA AGACAGATAC ATCCCACCAT
 121  GATCAGGATC ACCCAACCTT CAACAAGATC ACCCCCAACC TGGCTGAGTT CGCCTTCAGC
 181  CTATACCGCC AGCTGGCACA CCAGTCCAAC AGCACCAATA TCTTCTTCTC CCCAGTGAGC
 241  ATCGCTACAG CCTTTGCAAT GCTCTCCCTG GGGACCAAGG CTGACACTCA CGATGAAATC
 301  CTGGAGGGCC TGAATTTCAA CCTCACGGAG ATTCCGGAGG CTCAGATCCA TGAAGGCTTC
 361  CAGGAACTCC TCCGTACCCT CAACCAGCCA GACAGCCAGC TCCAGCTGAC CACCGGCAAT
 421  GGCCTGTTCC TCAGCGAGGG CCTGAAGCTA GTGGATAAGT TTTTGGAGGA TGTTAAAAAG
 481  TTGTACCACT CAGAAGCCTT CACTGTCAAC TTCGGGGACA CCGAAGAGGC CAAGAAACAG
 541  ATCAACGATT ACGTGGAGAA GGGTACTCAA GGGAAAATTG TGGATTTGGT CAAGGAGCTT
 601  GACAGAGACA CAGTTTTTGC TCTGGTGAAT TACATCTTCT TTAAAGGCAA ATGGGAGAGA
 661  CCCTTTGAAG TCAAGGACAC CGAGGAAGAG GACTTCCACG TGGACCAGGT GACCACCGTG
 721  AAGGTGCCTA TGATGAAGCG TTTAGGCATG TTTAACATCC AGCACTGTAA GAAGCTGTCC
 781  AGCTGGGTGC TGCTGATGAA ATACCTGGGC AATGCCACCG CCATCTTCTT CCTGCCTGAT
 841  GAGGGGAAAC TACAGCACCT GGAAAATGAA CTCACCCACG ATATCATCAC CAAGTTCCTG
 901  GAAAATGAAG ACAGAAGGTC TGCCAGCTTA CATTTACCCA AACTGTCCAT TACTGGAACC
 961  TATGATCTGA AGAGCGTCCT GGGTCAACTG GGCATCACTA AGGTCTTCAG CAATGGGGCT
1021  GACCTCTCCG GGGTCACAGA GGAGGCACCC CTGAAGCTCT CCAAGGCCGT GCATAAGGCT
```

```
1081  GTGCTGACCA TCGACGAGAA AGGGACTGAA GCTGCTGGGG CCATGTTTTT AGAGGCCATA

1141  CCCATGTCTA TCCCCCCCGA GGTCAAGTTC AACAAACCCT TTGTCTTCTT AATGATTGAA

1201  CAAAATACCA AGTCTCCCCT CTTCATGGGA AAAGTGGTGA ATCCCACCCA AAAACCATGG

1261  GGTGGAGGCG GTTCAAGAGG TCCTACGATC AAGCCCTGCC CGCCTAGATC TGACAAAACT

1321  CACACATGCC CACCGTGCCC AGCACCTGAA CTCCTGGGGG GACCGTCAGT CTTCCTCTTC

1381  CCCCCAAAAC CCAAGGACAC CCTCATGATC TCCCGGACCC CTGAGGTCAC ATGCGTGGTG

1441  GTGGACGTGA GCCACGAAGA CCCTGAGGTC AAGTTCAACT GGTACGTGGA CGGCGTGGAG

1501  GTGCATAATG CCAAGACAAA GCCGCGGGAG GAGCAGTACA ACAGCACGTA CCGTGTGGTC

1561  AGCGTCCTCA CCGTCCTGCA CCAGGACTGG CTGAATGGCA AGGAGTACAA GTGCAAGGTC

1621  TCCAACAAAG CCCTCCCAGC CCCCATCGAG AAACCATCT CCAAAGCCAA AGGGCAGCCC

1681  CGAGAACCAC AGGTGTACAC CCTGCCCCCA TCCCGGGAGG AGATGACCAA GAACCAGGTC

1741  AGCCTGACCT GCCTGGTCAA AGGCTTCTAT CCCAGCGACA TCGCCGTGGA GTGGGAGAGC

1801  AATGGGCAGC CGGAGAACAA CTACAAGACC ACGCCTCCCG TGCTGGACTC CGACGGCTCC

1861  TTCTTCCTCT ACAGCAAGCT CACCGTGGAC AAGAGCAGGT GGCAGCAGGG GAACGTCTTC

1921  TCATGCTCCG TGATGCACGA GGCTCTGCAC AACCACTACA CGCAGAAGAG CCTCTCCCTG

1981  TCTCCGGGTA AATAA (SEQ ID NO: 12)
   1  MPSSVSWGIL LLAGLCCLVP VSLAEDPQGD AAQKTDTSHH DQDHPTFNKI TPNLAEFAFS

61  LYRQLAHQSN STNIFFSPVS IATAFAMLSL GTKADTHDEI LEGLNFNLTE IPEAQIHEGF

121  QELLRTLNQP DSQLQLTTGN GLFLSEGLKL VDKFLEDVKK LYHSEAFTVN FGDTEEAKKQ

181  INDYVEKGTQ GKIVDLVKEL DRDTVFALVN YIFFKGKWER PFEVKDTEEE DFHVDQVTTV

241  KVPMMKRLGM FNIQHCKKLS SWVLLMKYLG NATAIFFLPD EGKLQHLENE LTHDIITKFL

301  ENEDRRSASL HLPKLSITGT YDLKSVLGQL GITKVFSNGA DLSGVTEEAP LKLSKAVHKA

361  VLTIDEKGTE AAGAMFLEAI PMSIPPEVKF NKPFVFLMIE QNTKSPLFMG KVVNPTQKPW

421  GGGGSRGPTI KPCPPRSDKT HTCPPCPAPE LLGGPSVFLF PPKPKDTLMI SRTPEVTCVV

481  VDVSHEDPEV KFNWYVDGVE VHNAKTKPRE EQYNSTYRVV SVLTVLHQDW LNGKEYKCKV

541  SNKALPAPIE KTISKAKGQP REPQVYTLPP SREEMTKNQV SLTCLVKGFY PSDIAVEWES

601  NGQPENNYKT TPPVLDSDGS FFLYSKLTVD KSRWQQGNVF SCSVMHEALH NHYTQKSLSL

661  SPGK
```

In one embodiment, an AAT polypeptide is conjugated to a non-lytic Fc region of IgG1 at the N-terminus of AAT with two GGGGS linkers ("Construct 4") (FIG. 2A). A nucleic acid sequence encoding an AAT polypeptide conjugated to a non-lytic Fc region of IgG1 at the N-terminus of AAT with two GGGGS linkers is provided as SEQ ID NO:13. The amino acid sequence encoded by SEQ ID NO:13 is provided as SEQ ID NO:14, which comprises an IL2 signal peptide sequence, the sequence of a non-lytic Fc region of IgG1, two GGGGS linkers, and the sequence of an AAT polypeptide.

```
                                                                 (SEQ ID NO: 13)
   1  ATGTACAGGA TGCAACTCCT GTCTTGCATT GCACTAAGTC TTGCACTTGT CACGAATTCG

61  GATATCGACA AAACTCACAC ATGCCCACCG TGCCCAGCAC CTGAACTCGA GGGGGGACCG

121  TCAGTCTTCC TCTTCCCCCC AAAACCCAAG GACACCCTCA TGATCTCCCG GACCCCTGAG

181  GTCACATGCG TGGTGGTGGA CGTGAGCCAC GAAGACCCTG AGGTCAAGTT CAACTGGTAC

241  GTGGACGGCG TGGAGGTGCA TAATGCCAAG ACAAAGCCGC GGGAGGAGCA GTACAACAGC

301  ACGTACCGTG TGGTCAGCGT CCTCACCGTC CTGCACCAGG ACTGGCTGAA TGGCAAGGCG

361  TACAAGGCCG CGGTCTCCAA CAAAGCCCTC CCAGCCCCCA TCGAGAAAAC CATCTCCAAA
```

```
                                                 -continued
 421    GCCAAGGGC AGCCCCGAGA ACCACAGGTG TACACCCTGC CCCCATCCCG GGAGGAGATG
 481    ACCAAGAACC AGGTCAGCCT GACCTGCCTG GTCAAAGGCT TCTATCCCAG CGACATCGCC
 541    GTGGAGTGGG AGAGCAATGG GCAGCCGGAG AACAACTACA AGACCACGCC TCCCGTGCTG
 601    GACTCCGACG GCTCCTTCTT CCTCTACAGC AAGCTCACCG TGGACAAGAG CAGGTGGCAG
 661    CAGGGGAACG TCTTCTCATG CTCCGTGATG CACGAGGCTC TGCACAACCA CTACACGCAG
 721    AAGAGCCTCT CCCTGTCTCC GGGTAAACCA TGGGGTGGAG GCGGTTCAGG CGGAGGTGGC
 781    TCTAGATCTG CTGCCCAGAA GACAGATACA TCCCACCATG ATCAGGATCA CCCAACCTTC
 841    AACAAGATCA CCCCCAACCT GGCTGAGTTC GCCTTCAGCC TATACCGCCA GCTGGCACAC
 901    CAGTCCAACA GCACCAATAT CTTCTTCTCC CCAGTGAGCA TCGCTACAGC CTTTGCAATG
 961    CTCTCCCTGG GGACCAAGGC TGACACTCAC GATGAAATCC TGGAGGGCCT GAATTTCAAC
1021    CTCACGGAGA TTCCGGAGGC TCAGATCCAT GAAGGCTTCC AGGAACTCCT CCGTACCCTC
1081    AACCAGCCAG ACAGCCAGCT CCAGCTGACC ACCGGCAATG GCCTGTTCCT CAGCGAGGGC
1141    CTGAAGCTAG TGGATAAGTT TTTGGAGGAT GTTAAAAAGT TGTACCACTC AGAAGCCTTC
1201    ACTGTCAACT TCGGGGACAC CGAAGAGGCC AAGAAACAGA TCAACGATTA CGTGGAGAAG
1261    GGTACTCAAG GGAAAATTGT GGATTTGGTC AAGGAGCTTG ACAGAGACAC AGTTTTTGCT
1321    CTGGTGAATT ACATCTTCTT TAAAGGCAAA TGGGAGAGAC CCTTTGAAGT CAAGGACACC
1381    GAGGAAGAGG ACTTCCACGT GGACCAGGTG ACCACCGTGA AGGTGCCTAT GATGAAGCGT
1441    TTAGGCATGT TTAACATCCA GCACTGTAAG AAGCTGTCCA GCTGGGTGCT GCTGATGAAA
1501    TACCTGGGCA ATGCCACCGC CATCTTCTTC CTGCCTGATG AGGGGAAACT ACAGCACCTG
1561    GAAAATGAAC TCACCCACGA TATCATCACC AAGTTCCTGG AAAATGAAGA CAGAAGGTCT
1621    GCCAGCTTAC ATTTACCCAA ACTGTCCATT ACTGGAACCT ATGATCTGAA GAGCGTCCTG
1681    GGTCAACTGG GCATCACTAA GGTCTTCAGC AATGGGGCTG ACCTCTCCGG GGTCACAGAG
1741    GAGGCACCCC TGAAGCTCTC CAAGGCCGTG CATAAGGCTG TGCTGACCAT CGACGAGAAA
1801    GGGACTGAAG CTGCTGGGGC CATGTTTTTA GAGGCCATAC CCATGTCTAT CCCCCCCGAG
1861    GTCAAGTTCA ACAAACCCTT TGTCTTCTTA ATGATTGAAC AAAATACCAA GTCTCCCCTC
1921    TTCATGGGAA AAGTGGTGAA TCCCACCCAA AAATAA
                                                                    (SEQ ID NO: 14)
   1    MYRMQLLSCI ALSLALVTNS DIDKTHTCPP CPAPELEGGP SVFLFPPKPK DTLMISRTPE
  61    VTCVVVDVSH EDPEVKFNWY VDGVEVHNAK TKPREEQYNS TYRVVSVLTV LHQDWLNGKA
 121    YKAAVSNKAL PAPIEKTISK AKGQPREPQV YTLPPSREEM TKNQVSLTCL VKGFYPSDIA
 181    VEWESNGQPE NNYKTTPPVL DSDGSFFLYS KLTVDKSRWQ QGNVFSCSVM HEALHNHYTQ
 241    KSLSLSPGKP WGGGGSGGGG SRSAAQKTDT SHHDQDHPTF NKITPNLAEF AFSLYRQLAH
 301    QSNSTNIFFS PVSIATAFAM LSLGTKADTH DEILEGLNFN LTEIPEAQIH EGFQELLRTL
 361    NQPDSQLQLT TGNGLFLSEG LKLVDKFLED VKKLYHSEAF TVNFGDTEEA KKQINDYVEK
 421    GTQGKIVDLV KELDRDTVFA LVNYIFFKGK WERPFEVKDT EEEDFHVDQV TTVKVPMMKR
 481    LGMFNIQHCK KLSSWVLLMK YLGNATAIFF LPDEGKLQHL ENELTHDIIT KFLENEDRRS
 541    ASLHLPKLSI TGTYDLKSVL GQLGITKVFS NGADLSGVTE EAPLKLSKAV HKAVLTIDEK
 601    GTEAAGAMFL EAIPMSIPPE VKFNKPFVFL MIEQNTKSPL FMGKVVNPTQ K
```

In one embodiment, the AAT polypeptide is directly conjugated to a non-lytic Fc region of IgG1 at the C-terminus of AAT ("Construct 5") (FIG. 2B). A nucleic acid sequence encoding an AAT polypeptide directly conjugated to a non-lytic Fc region of IgG1 at the C terminus of AAT is provided as SEQ ID NO:15. The amino acid sequence encoded by SEQ ID NO:15 is provided as SEQ ID NO:16, which comprises the sequence of an AAT polypeptide, an IgG1 hinge sequence, and the sequence of a non-lytic Fc region of IgG1.

```
                                                        (SEQ ID NO: 15)
   1   ATGCCGTCTT CTGTCTCGTG GGGCATCCTC CTGCTGGCAG GCCTGTGCTG CCTGGTCCCT
  61   GTCTCCCTGG CTGAGGATCC CCAGGGAGAT GCTGCCCAGA AGACAGATAC ATCCCACCAT
 121   GATCAGGATC ACCCAACCTT CAACAAGATC ACCCCCAACC TGGCTGAGTT CGCCTTCAGC
 181   CTATACCGCC AGCTGGCACA CCAGTCCAAC AGCACCAATA TCTTCTTCTC CCCAGTGAGC
 241   ATCGCTACAG CCTTTGCAAT GCTCTCCCTG GGACCAAGG CTGACACTCA CGATGAAATC
 301   CTGGAGGGCC TGAATTTCAA CCTCACGGAG ATTCCGGAGG CTCAGATCCA TGAAGGCTTC
 361   CAGGAACTCC TCCGTACCCT CAACCAGCCA GACAGCCAGC TCCAGCTGAC CACCGGCAAT
 421   GGCCTGTTCC TCAGCGAGGG CCTGAAGCTA GTGGATAAGT TTTTGGAGGA TGTTAAAAAG
 481   TTGTACCACT CAGAAGCCTT CACTGTCAAC TTCGGGGACA CCGAAGAGGC CAAGAAACAG
 541   ATCAACGATT ACGTGGAGAA GGGTACTCAA GGGAAAATTG TGGATTTGGT CAAGGAGCTT
 601   GACAGAGACA CAGTTTTTGC TCTGGTGAAT TACATCTTCT TTAAAGGCAA ATGGGAGAGA
 661   CCCTTTGAAG TCAAGGACAC CGAGGAAGAG GACTTCCACG TGGACCAGGT GACCACCGTG
 721   AAGGTGCCTA TGATGAAGCG TTTAGGCATG TTTAACATCC AGCACTGTAA GAAGCTGTCC
 781   AGCTGGGTGC TGCTGATGAA ATACCTGGGC AATGCCACCG CCATCTTCTT CCTGCCTGAT
 841   GAGGGGAAAC TACAGCACCT GGAAAATGAA CTCACCCACG ATATCATCAC CAAGTTCCTG
 901   GAAAATGAAG ACAGAAGGTC TGCCAGCTTA CATTTACCCA AACTGTCCAT TACTGGAACC
 961   TATGATCTGA AGAGCGTCCT GGGTCAACTG GCATCACTA AGGTCTTCAG CAATGGGGCT
1021   GACCTCTCCG GGGTCACAGA GGAGGCACCC CTGAAGCTCT CCAAGGCCGT GCATAAGGCT
1081   GTGCTGACCA TCGACGAGAA AGGGACTGAA GCTGCTGGGG CCATGTTTTT AGAGGCCATA
1141   CCCATGTCTA TCCCCCCCGA GGTCAAGTTC AACAAACCCT TTGTCTTCTT AATGATTGAA
1201   CAAAATACCA AGTCTCCCCT CTTCATGGGA AAAGTGGTGA ATCCCACCCA AAAACCATGG
1261   AGAGGTCCTA CGATCAAGCC CTGCCCGCCT AGATCTGACA AAACTCACAC ATGCCCACCG
1321   TGCCCAGCAC CTGAACTCGA GGGGGGACCG TCAGTCTTCC TCTTCCCCCC AAAACCCAAG
1381   GACACCCTCA TGATCTCCCG GACCCCTGAG GTCACATGCG TGGTGGTGGA CGTGAGCCAC
1441   GAAGACCCTG AGGTCAAGTT CAACTGGTAC GTGGACGGCG TGGAGGTGCA TAATGCCAAG
1501   ACAAAGCCGC GGGAGGAGCA GTACAACAGC ACGTACCGTG TGGTCAGCGT CCTCACCGTC
1561   CTGCACCAGG ACTGGCTGAA TGGCAAGGCG TACAAGGCCG GGTCTCCAA CAAAGCCCTC
1621   CCAGCCCCCA TCGAGAAAAC CATCTCCAAA GCCAAAGGGC AGCCCCGAGA ACCACAGGTG
1681   TACACCCTGC CCCCATCCCG GGAGGAGATG ACCAAGAACC AGGTCAGCCT GACCTGCCTG
1741   GTCAAAGGCT TCTATCCCAG CGACATCGCC GTGGAGTGGG AGAGCAATGG GCAGCCGGAG
1801   AACAACTACA AGACCACGCC TCCCGTGCTG GACTCCGACG GCTCCTTCTT CCTCTACAGC
1861   AAGCTCACCG TGGACAAGAG CAGGTGGCAG CAGGGGAACG TCTTCTCATG CTCCGTGATG
1921   CACGAGGCTC TGCACAACCA CTACACGCAG AAGAGCCTCT CCCTGTCTCC GGGTAAATAA
                                                        (SEQ ID NO: 16)
   1   MPSSVSWGIL LLAGLCCLVP VSLAEDPQGD AAQKTDTSHH DQDHPTFNKI TPNLAEFAFS
  61   LYRQLAHQSN STNIFFSPVS IATAFAMLSL GTKADTHDEI LEGLNFNLTE IPEAQIHEGF
 121   QELLRTLNQP DSQLQLTTGN GLFLSEGLKL VDKFLEDVKK LYHSEAFTVN FGDTEEAKKQ
 181   INDYVEKGTQ GKIVDLVKEL DRDTVFALVN YIFFKGKWER PFEVKDTEEE DFHVDQVTTV
 241   KVPMMKRLGM FNIQHCKKLS SWVLLMKYLG NATAIFFLPD EGKLQHLENE LTHDIITKFL
 301   ENEDRRSASL HLPKLSITGT YDLKSVLGQL GITKVFSNGA DLSGVTEEAP LKLSKAVHKA
 361   VLTIDEKGTE AAGAMFLEAI PMSIPPEVKF NKPFVFLMIE QNTKSPLFMG KVVNPTQKPW
```

```
421  RGPTIKPCPP RSDKTHTCPP CPAPELEGGP SVFLFPPKPK DTLMISRTPE VTCVVVDVSH

481  EDPEVKFNWY VDGVEVHNAK TKPREEQYNS TYRVVSVLTV LHQDWLNGKA YKAAVSNKAL

541  PAPIEKTISK AKGQPREPQV YTLPPSREEM TKNQVSLTCL VKGFYPSDIA VEWESNGQPE

601  NNYKTTPPVL DSDGSFFLYS KLTVDKSRWQ QGNVFSCSVM HEALHNHYTQ KSLSLSPGK
```

In yet another embodiment, the AAT polypeptide is conjugated to a non-lytic Fc region of IgG1 at the C-terminus of AAT with one GGGGS linker ("Construct 6") (FIG. 2C). A nucleic acid sequence encoding an exemplary AAT polypeptide conjugated to a non-lytic Fc region of IgG1 at the C-terminus of AAT with one GGGGS linker is provided as SEQ ID NO:17. The amino acid sequence encoded by SEQ ID NO:17 is provided as SEQ ID NO:18, which comprises the sequence of an AAT polypeptide, a GGGGS linker, an IgG1 hinge sequence, and the sequence of a non-lytic Fc region of IgG1.

```
                                                          (SEQ ID NO: 17)
   1  ATGCCGTCTT CTGTCTCGTG GGGCATCCTC CTGCTGGCAG GCCTGTGCTG CCTGGTCCCT

61  GTCTCCCTGG CTGAGGATCC CCAGGGAGAT GCTGCCCAGA AGACAGATAC ATCCCACCAT

121  GATCAGGATC ACCCAACCTT CAACAAGATC ACCCCCAACC TGGCTGAGTT CGCCTTCAGC

181  CTATACCGCC AGCTGGCACA CCAGTCCAAC AGCACCAATA TCTTCTTCTC CCCAGTGAGC

241  ATCGCTACAG CCTTTGCAAT GCTCTCCCTG GGGACCAAGG CTGACACTCA CGATGAAATC

301  CTGGAGGGCC TGAATTTCAA CCTCACGGAG ATTCCGGAGG CTCAGATCCA TGAAGGCTTC

361  CAGGAACTCC TCCGTACCCT CAACCAGCCA GACAGCCAGC TCCAGCTGAC CACCGGCAAT

421  GGCCTGTTCC TCAGCGAGGG CCTGAAGCTA GTGGATAAGT TTTTGGAGGA TGTTAAAAAG

481  TTGTACCACT CAGAAGCCTT CACTGTCAAC TTCGGGGACA CCGAAGAGGC CAAGAAACAG

541  ATCAACGATT ACGTGGAGAA GGGTACTCAA GGGAAAATTG TGGATTTGGT CAAGGAGCTT

601  GACAGAGACA CAGTTTTTGC TCTGGTGAAT TACATCTTCT TTAAAGGCAA ATGGGAGAGA

661  CCCTTTGAAG TCAAGGACAC CGAGGAAGAG GACTTCCACG TGGACCAGGT GACCACCGTG

721  AAGGTGCCTA TGATGAAGCG TTTAGGCATG TTTAACATCC AGCACTGTAA GAAGCTGTCC

781  AGCTGGGTGC TGCTGATGAA ATACCTGGGC AATGCCACCG CCATCTTCTT CCTGCCTGAT

841  GAGGGGAAAC TACAGCACCT GGAAAATGAA CTCACCCACG ATATCATCAC CAAGTTCCTG

901  GAAAATGAAG ACAGAAGGTC TGCCAGCTTA CATTTACCCA AACTGTCCAT TACTGGAACC

961  TATGATCTGA AGAGCGTCCT GGGTCAACTG GGCATCACTA AGGTCTTCAG CAATGGGGCT

1021  GACCTCTCCG GGGTCACAGA GGAGGCACCC CTGAAGCTCT CCAAGGCCGT GCATAAGGCT

1081  GTGCTGACCA TCGACGAGAA AGGGACTGAA GCTGCTGGGG CCATGTTTTT AGAGGCCATA

1141  CCCATGTCTA TCCCCCCCGA GGTCAAGTTC AACAAACCCT TTGTCTTCTT AATGATTGAA

1201  CAAAATACCA AGTCTCCCCT CTTCATGGGA AAAGTGGTGA ATCCCACCCA AAAACCATGG

1261  GGTGGAGGCG GTTCAAGAGG TCCTACGATC AAGCCCTGCC CGCCTAGATC TGACAAAACT

1321  CACACATGCC CACCGTGCCC AGCACCTGAA CTCGAGGGGG GACCGTCAGT CTTCCTCTTC

1381  CCCCCAAAAC CCAAGGACAC CCTCATGATC TCCCGGACCC CTGAGGTCAC ATGCGTGGTG

1441  GTGGACGTGA GCCACGAAGA CCCTGAGGTC AAGTTCAACT GGTACGTGGA CGGCGTGGAG

1501  GTGCATAATG CCAAGACAAA GCCGCGGGAG GAGCAGTACA ACAGCACGTA CCGTGTGGTC

1561  AGCGTCCTCA CCGTCCTGCA CCAGGACTGG CTGAATGGCA AGGCGTACAA GGCCGCGGTC

1621  TCCAACAAAG CCCTCCCAGC CCCCATCGAG AAAACCATCT CCAAAGCCAA AGGGCAGCCC

1681  CGAGAACCAC AGGTGTACAC CCTGCCCCCA TCCCGGGAGG AGATGACCAA GAACCAGGTC

1741  AGCCTGACCT GCCTGGTCAA AGGCTTCTAT CCCAGCGACA TCGCCGTGGA GTGGGAGAGC
```

```
-continued
1801    AATGGGCAGC  CGGAGAACAA  CTACAAGACC  ACGCCTCCCG  TGCTGGACTC  CGACGGCTCC

1861    TTCTTCCTCT  ACAGCAAGCT  CACCGTGGAC  AAGAGCAGGT  GGCAGCAGGG  GAACGTCTTC

1921    TCATGCTCCG  TGATGCACGA  GGCTCTGCAC  AACCACTACA  CGCAGAAGAG  CCTCTCCCTG

1981    TCTCCGGGTA  AATAA (SEQ ID NO: 18)
   1    MPSSVSWGIL  LLAGLCCLVP  VSLAEDPQGD  AAQKTDTSHH  DQDHPTFNKI  TPNLAEFAFS

61    LYRQLAHQSN  STNIFFSPVS  IATAFAMLSL  GTKADTHDEI  LEGLNFNLTE  IPEAQIHEGF

121    QELLRTLNQP  DSQLQLTTGN  GLFLSEGLKL  VDKFLEDVKK  LYHSEAFTVN  FGDTEEAKKQ

181    INDYVEKGTQ  GKIVDLVKEL  DRDTVFALVN  YIFFKGKWER  PFEVKDTEEE  DFHVDQVTTV

241    KVPMMKRLGM  FNIQHCKKLS  SWVLLMKYLG  NATAIFFLPD  EGKLQHLENE  LTHDIITKFL

301    ENEDRRSASL  HLPKLSITGT  YDLKSVLGQL  GITKVFSNGA  DLSGVTEEAP  LKLSKAVHKA

361    VLTIDEKGTE  AAGAMFLEAI  PMSIPPEVKF  NKPFVFLMIE  QNTKSPLFMG  KVVNPTQKPW

421    GGGGSRGPTI  KPCPPRSDKT  HTCPPCPAPE  LEGGPSVFLF  PPKPKDTLMI  SRTPEVTCVV

481    VDVSHEDPEV  KFNWYVDGVE  VHNAKTKPRE  EQYNSTYRVV  SVLTVLHQDW  LNGKAYKAAV

541    SNKALPAPIE  KTISKAKGQP  REPQVYTLPP  SREEMTKNQV  SLTCLVKGFY  PSDIAVEWES

601    NGQPENNYKT  TPPVLDSDGS  FFLYSKLTVD  KSRWQQGNVF  SCSVMHEALH  NHYTQKSLSL

661    SPGK
```

AAT-Fc nucleic acids described herein include both DNA and RNA, including genomic DNA and synthetic (e.g., chemically synthesized) DNA. Nucleic acids can be double-stranded or single-stranded. Where single-stranded, the nucleic acid can be a sense strand or an antisense strand. Nucleic acids can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

The term "isolated nucleic acid" means a nucleic acid, e.g., DNA or RNA, that is not immediately contiguous with both of the coding sequences with which it is immediately contiguous (one on the 5' end and one on the 3' end) in the naturally occurring genome of the organism from which it is derived. Thus, in one embodiment, an isolated AAT-Fc nucleic acid includes some or all of the 5' non-coding (e.g., promoter) sequences that are immediately contiguous to the AAT nucleic acid coding sequence. The term includes, for example, recombinant DNA that is incorporated into a vector, into an autonomously replicating plasmid or virus, or into the genomic DNA of a prokaryote or eukaryote, or which exists as a separate molecule (e.g., a genomic DNA fragment produced by PCR or restriction endonuclease treatment) independent of other sequences. It also includes a recombinant DNA that is part of a hybrid gene encoding an additional polypeptide sequence.

The invention includes vectors, preferably expression vectors, containing a nucleic acid that encodes the fusion proteins described herein. As used herein, the term "vector" refers to a nucleic acid molecule capable of transporting another nucleic acid to which it has been linked and can include, e.g., a plasmid, cosmid, or viral vector. The vector can autonomously replicate or it can integrate into a host cell's DNA. Viral vectors include, e.g., replication-defective retroviruses, adenoviruses, and adeno-associated viruses.

Figure 3:
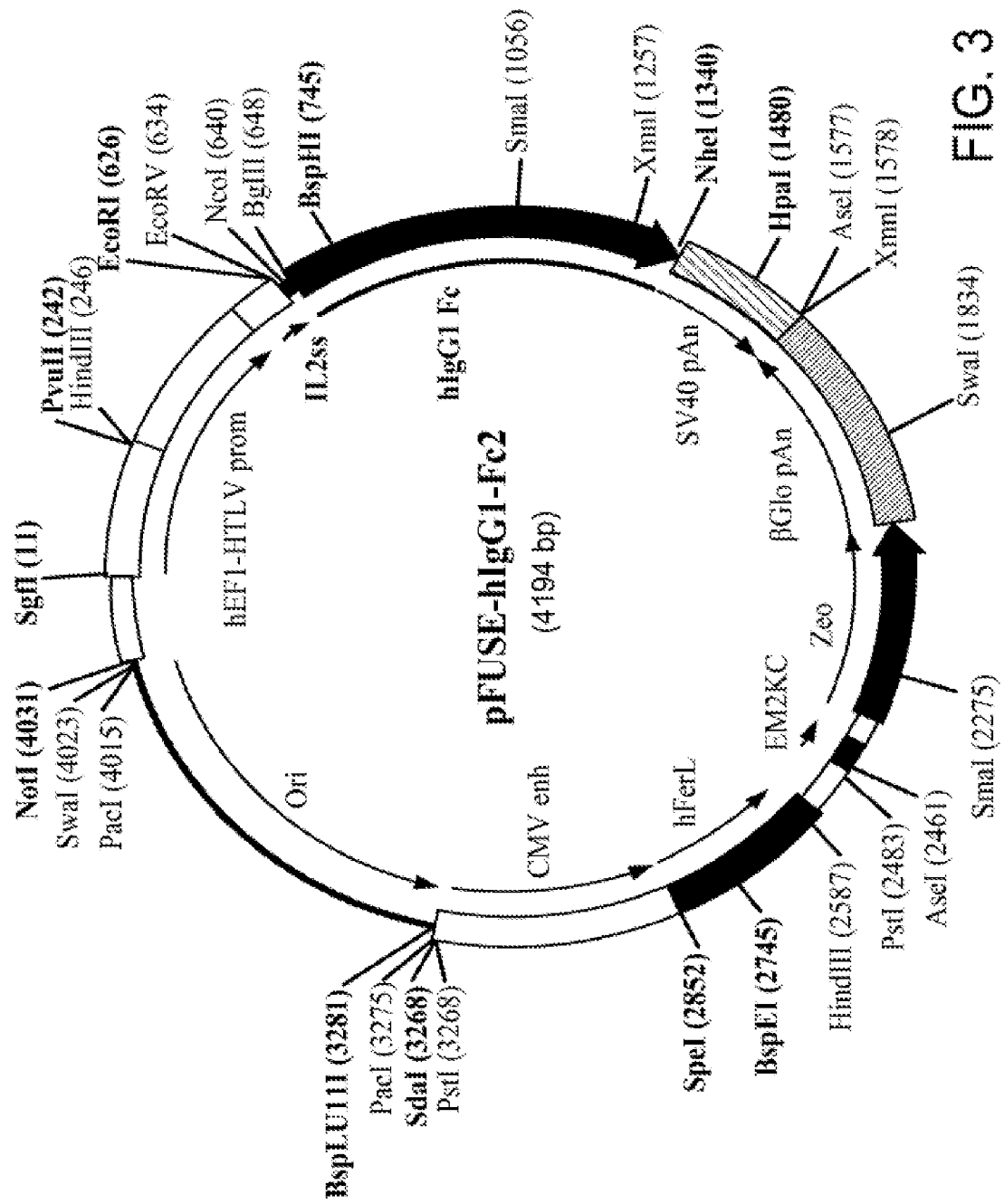
FIG. 3 is a map of a pFUSE expression vector used to express AAT conjugated to a Fc region of an IgG.

A vector can include an AAT-Fc nucleic acid in a form suitable for expression of the nucleic acid in a host cell (FIG. 3). Preferably a recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce AAT-Fc polypeptides encoded by nucleic acids as described herein.

The recombinant expression vectors of the invention can be designed for expression of AAT-Fc polypeptides in prokaryotic or eukaryotic cells. For example, polypeptides of the invention can be expressed in E. coli, insect cells (e.g., using baculovirus expression vectors), yeast cells, or mammalian cells (e.g., CHO or COS cells). Suitable host cells are discussed further in Goeddel, (1990) Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, Gene 67:31-40, 1988), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

One can maximize recombinant protein expression in *E. coli* by expressing the protein in host bacteria with an impaired capacity to proteolytically cleave the recombinant protein (Gottesman (1990) Gene Expression Technology: Methods in Enzymology 185:119-128, Academic Press, San Diego, Calif.). Another strategy is to alter the nucleic acid sequence of the nucleic acid to be inserted into an expression vector so that the individual codons for each amino acid are those preferentially utilized in *E. coli* (Wada et al., Nucleic Acids Res 20:2111-2118, 1992). Such alteration of nucleic acid sequences of the invention can be carried out by standard DNA synthesis techniques.

Modified versions of peptides disclosed herein are referred to as "peptide derivatives," and they can also be used in the new methods. For example, peptide derivatives of a peptide can be used instead of that peptide in therapeutic methods described herein. Peptides disclosed herein can be modified according to the methods known in the art for producing peptidomimetics. See, e.g., Kazmierski, W. M., ed., *Peptidomimetics Protocols*, Human Press (Totowa N.J. 1998); Goodman et al., eds., *Houben-Weyl Methods of Organic Chemistry: Synthesis of Peptides and Peptidomimetics*, Thiele Verlag (New York 2003); and Mayo et al., *J Biol Chem* 278:45746, 2003. In some cases, these modified peptidomimetic versions of the peptides and fragments disclosed herein exhibit enhanced stability in vivo, relative to the non-peptidomimetic peptides.

Methods for creating a peptidomimetic include substituting one or more, e.g., all, of the amino acids in a peptide sequence with D-amino acid enantiomers. Such sequences are referred to herein as "retro" sequences. In another method, the N-terminal to C-terminal order of the amino acid residues is reversed, such that the order of amino acid residues from the N-terminus to the C-terminus of the original peptide becomes the order of amino acid residues from the C-terminus to the N-terminus in the modified peptidomimetic. Such sequences can be referred to as "inverso" sequences.

Peptidomimetics can be both the retro and inverso versions, i.e., the "retro-inverso" version of a peptide disclosed herein. The new peptidomimetics can be composed of D-amino acids arranged so that the order of amino acid residues from the N-terminus to the C-terminus in the peptidomimetic corresponds to the order of amino acid residues from the C-terminus to the N-terminus in the original peptide.

Other methods for making a peptidomimetics include replacing one or more amino acid residues in a peptide with a chemically distinct but recognized functional analog of the amino acid, i.e., an artificial amino acid analog. Artificial amino acid analogs include β-amino acids, β-substituted β-amino acids ("β³-amino acids"), phosphorous analogs of amino acids, such as α-amino phosphonic acids, and α-amino phosphinic acids, and amino acids having non-peptide linkages. Artificial amino acids can be used to create peptidomimetics, such as peptoid oligomers (e.g., peptoid amide or ester analogues), β-peptides, cyclic peptides, oligourea or oligocarbamate peptides; or heterocyclic ring molecules.

The term "purified" refers to a nucleic acid or polypeptide (e.g., an AAT-Fc nucleic acid or AAT-Fc polypeptide) that is substantially free of cellular or viral material with which it is naturally associated, or culture medium (when produced by recombinant DNA techniques), or chemical precursors or other chemicals (when chemically synthesized). Moreover, an isolated nucleic acid fragment is a nucleic acid fragment that is not naturally occurring as a fragment and would not be found in the natural state. In some embodiments, the invention includes nucleic acid sequences that are substantially identical to an AAT nucleic acid and to a nucleic acid encoding an Fc region of an immunoglobulin, e.g., an Fc region of an IgG1. A nucleic acid sequence that is "substantially identical" to an AAT nucleic acid is at least 90% identical (e.g., at least or about 92%, 95%, 96%, 97%, 98%, 99%, or 100% identical) to the AAT nucleic acid sequence represented by SEQ ID NO:1. A nucleic acid sequence that is "substantially identical" to a nucleic acid encoding an Fc region of an IgG1 is at least 90% identical (e.g., at least or about 92%, 95%, 96%, 97%, 98%, 99%, or 100% identical) to the nucleic acid sequence represented by SEQ ID NO:3 or 5. For purposes of comparison of nucleic acids, the length of the reference nucleic acid sequence will be at least 50 nucleotides, but can be longer, e.g., at least 60 or more nucleotides.

To determine the percent identity of two amino acid or nucleic acid sequences, the sequences are aligned for optimal comparison purposes (i.e., gaps can be introduced as required in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., percent identity=# of identical positions/total # of overlapping positions×100). The two sequences may be of the same length.

The percent identity or homology between two sequences can be determined using a mathematical algorithm. A non-limiting example of a mathematical algorithm utilized for the comparison of two sequences is the algorithm of Karlin and Altschul, *Proc Natl Acad Sci USA* 87:2264-2268, 1990, modified as in Karlin and Altschul, *Proc Natl Acad Sci USA* 90:5873-5877, 1993. Such an algorithm is incorporated into the NBLAST and XBLAST programs of Altschul et al., *J Mol Biol* 215:403-410, 1990. BLAST nucleotide searches can be performed with the NBLAST program, score=100, wordlength=12 to obtain nucleotide sequences homologous to AAT nucleic acid molecules of the invention. BLAST protein searches can be performed with the) XBLAST program, score=50, wordlength=3 to obtain amino acid sequences homologous to AAT protein molecules of the invention. To obtain gapped alignments for comparison purposes, Gapped BLAST can be utilized as described in Altschul et al., Nucleic Acids Res. 25:3389-3402, 1997. When utilizing BLAST and Gapped BLAST programs, the default parameters of the respective programs (e.g., XBLAST and NBLAST) can be used. See online at ncbi.nlm.nih.gov.

In other embodiments, the invention includes variants, homologs, and/or fragments of certain AAT nucleic acids, e.g., variants, homologs, and/or fragments of the AAT nucleic acid sequences represented by SEQ ID NO:1. The terms "variant" or "homolog" in relation to AAT nucleic acids include any substitution, variation, modification, replacement, deletion, or addition of one (or more) nucleotides from or to the sequence of an AAT nucleic acid. The resultant nucleotide sequence may encode an AAT polypeptide that has at least 50% of a biological activity (e.g., inhibition of elastase) of the referenced AAT polypeptides (e.g., SEQ ID NO:2). In particular, the term "homolog" covers homology with respect to structure and/or function as long as the resultant nucleotide sequence encodes or is capable of encoding an AAT polypeptide that has at least 50% of the biological activity of AAT encoded by a sequence shown herein as SEQ ID NO:1. With respect to sequence homology, there is at least 75% (e.g., 85%, 90%, 95%, 96%, 97%, 98%, 99%, or 100%) homology to the sequence shown as SEQ ID NO:1. The term "homology" as used herein can be equated with the term "identity."

"Substantial homology" or "substantially homologous," where homology indicates sequence identity, means at least 90% identical (e.g., at least about 92%, 95%, 96%, 97%, 98%, or 99%) sequence identity, as judged by direct sequence alignment and comparison. "Substantial homology" when assessed by the BLAST algorithm equates to sequences which match with an EXPECT value of at least about 7, e.g., at least about 9, 10, or more. The default threshold for EXPECT in BLAST searching is usually 10.

Also included within the scope of the present invention are certain alleles of certain AAT genes. As used herein, an "allele" or "allelic sequence" is an alternative form of AAT. Alleles can result from changes in the nucleotide sequence, and generally produce altered mRNAs or polypeptides whose structure or function may or may not be altered. Any given gene can have none, one, or more than one allelic form. Common changes that give rise to alleles are generally ascribed to deletions, additions, or substitutions of amino acids. Each of these types of changes can occur alone, or in combination with the others, one or more times in a given sequence.

The invention also includes nucleic acids that hybridize, e.g., under stringent hybridization conditions (as defined herein) to all or a portion of the nucleotide sequences represented by SEQ ID NO:1, or a complement thereof. The hybridizing portion of the hybridizing nucleic acids is typically at least 15 (e.g., 20, 30, or 50) nucleotides in length. The hybridizing portion of the hybridizing nucleic acid is at least about 75%, e.g., at least about 80%, 90%, 92%, 95%, 96%, 97%, 98%, 99%, or 100% identical to the sequence of a portion or all of a nucleic acid encoding an AAT polypeptide, or to its complement. Hybridizing nucleic acids of the type described herein can be used as a cloning probe, a primer (e.g., a PCR primer), or a diagnostic probe. Nucleic acids that hybridize to the nucleotide sequence represented by SEQ ID NO:1, are considered "antisense oligonucleotides."

High stringency conditions are hybridizing at 68° C. in 5×SSC/5×Denhardt's solution/1.0% SDS, or in 0.5 M NaHPO$_4$ (pH 7.2)/1 mM EDTA/7% SDS, or in 50% formamide/0.25 M NaHPO$_4$ (pH 7.2)/0.25 M NaCl/1 mM EDTA/7% SDS; and washing in 0.2×SSC/0.1% SDS at room temperature or at 42° C., or in 0.1×SSC/0.1% SDS at 68° C., or in 40 mM NaHPO$_4$ (pH 7.2)/1 mM EDTA/5% SDS at 50° C., or in 40 mM NaHPO$_4$ (pH 7.2) 1 mM EDTA/1% SDS at 50° C. Stringent conditions include washing in 3×SSC at 42° C. The parameters of salt concentration and temperature can be varied to achieve the optimal level of identity between the probe and the target nucleic acid. Additional guidance regarding such conditions is available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

Also included in the invention are genetic constructs (e.g., vectors and plasmids) that include an AAT-Fc nucleic acid described herein, operably linked to a transcription and/or translation sequence to enable expression, e.g., expression vectors. A selected nucleic acid, e.g., a DNA molecule encoding an AAT-Fc polypeptide, is "operably linked" to another nucleic acid molecule, e.g., a promoter, when it is positioned either adjacent to the other molecule or in the same or other location such that the other molecule can control transcription and/or translation of the selected nucleic acid.

Also included in the invention are various engineered cells, e.g., transformed host cells, which contain an AAT-Fc nucleic acid described herein. A transformed cell is a cell into which (or into an ancestor of which) has been introduced, by means of recombinant DNA techniques, a nucleic acid encoding an AAT polypeptide. Both prokaryotic and eukaryotic cells are included. Mammalian cells transformed with an AAT-Fc nucleic acid can include host cells for an attaching enteric organism, e.g., intestinal cells, HeLa cells, and mouse embryonic fibroblasts. Prokaryotic cells can include bacteria, e.g., *Escherichia coli*. An engineered cell exemplary of the type included in the invention is an *E. coli* strain that expresses AAT.

Certain chimeric AAT polypeptides are included within the present invention. Examples of such chimeric AAT polypeptides are AAT polypeptides and fragments, such as the one shown as SEQ ID NO:2 conjugated to an Fc region of an immunoglobulin, e.g., IgG1, shown as SEQ ID NO:4 and 6. Also included within the present invention are certain fragments of AAT polypeptides, e.g., fragments of AAT polypeptides may inhibit elastase, or other useful portions of a full-length AAT polypeptide. For example, useful fragments of AAT polypeptides include, but are not limited to, fragments having elastase-inhibiting activity, and portions of such fragments.

The terms "protein" and "polypeptide" both refer to any chain of amino acids, regardless of length or post-translational modification (e.g., glycosylation or phosphorylation). Thus, the term "AAT" includes full-length naturally occurring isolated proteins, as well as recombinantly or synthetically produced polypeptides that correspond to the full-length naturally occurring proteins, or to a fragment of the full-length naturally occurring or synthetic polypeptide. Fragments of a protein can be produced by any of a variety of methods known to those skilled in the art, e.g., recombinantly, by proteolytic digestion, and/or by chemical synthesis. Internal or terminal fragments of a polypeptide can be generated by removing one or more nucleotides from one end (for a terminal fragment) or both ends (for an internal fragment) of a nucleic acid that encodes the polypeptide. Expression of such mutagenized DNA can produce polypeptide fragments. Digestion with "end-nibbling" endonucleases can thus generate DNAs that encode an array of fragments. DNAs that encode fragments of a protein can also be generated, e.g., by random shearing, restriction digestion, chemical synthesis of oligonucleotides, amplification of DNA using the polymerase chain reaction, or a combination of the above-discussed methods. Fragments can also be chemically synthesized using techniques known in the art, e.g., conventional Merrifield solid phase FMOC or t-Boc chemistry. For example, peptides of the present invention can be arbitrarily divided into fragments of desired length with no overlap of the fragments, or divided into overlapping fragments of a desired length.

A purified or isolated compound is a composition that is at least 75% by weight the compound of interest, e.g., AAT. In general, the preparation is at least 80% (e.g., at least 90%, 91%, 92%, 93%, 94%, 95%, 96%, 97%, 98%, 99%, or 100%) by weight the compound of interest. Purity can be measured by any appropriate standard method, e.g., column chromatography, polyacrylamide gel electrophoresis, or HPLC analysis.

In certain embodiments, AAT includes sequences substantially identical to all or portions of a naturally occurring AAT polypeptide. Polypeptides "substantially identical" to the AAT polypeptide sequences described herein have an amino acid sequence that is at least 75% (e.g., at least 80%, 90%, 91%, 92%, 93%, 94%, 95%, 96%, 97%, 98%, 99%, or 100%) identical to the amino acid sequences of the AAT polypeptides represented by SEQ ID NO:2 (measured as described herein). For purposes of comparison, the length of the reference AAT polypeptide sequence is at least 50 amino acids, e.g., at least 60, 80, 100, 200, 300, 394, or 418 amino acids.

In the case of polypeptide sequences that are less than 100% identical to a reference sequence, the non-identical positions are preferably, but not necessarily, conservative substitutions for the reference sequence. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Where a particular polypeptide is said to have a specific percent identity to a reference polypeptide of a defined length, the percent identity is relative to the reference polypeptide. Thus, a polypeptide that has 50% identity to a reference polypeptide that is 100 amino acids long can be a 50 amino acid polypeptide that is completely identical to a 50 amino acid long portion of the reference polypeptide. It also might be a 100 amino acid long polypeptide that has 50% identity to the reference polypeptide over its entire length.

Skilled practitioners can readily produce such molecules from, for example, an IgG2a-secreting hybridoma (e.g., HB129) or other eukaryotic cells or baculovirus systems. As noted and if desired, the Fc region can be mutated to inhibit its ability to fix complement and bind the Fc receptor. For murine IgG Fc, substitution of Ala residues for Glu 318, Lys 320, and Lys 322 renders the protein unable to direct ADCC. Substitution of Glu for Leu 235 inhibits the ability of the protein to bind the Fc receptor. Appropriate mutations for human IgG also are known (see, e.g., Morrison et al., *The Immunologist*, 2:119-124, 1994 and Brekke et al., *The Immunologist*, 2:125, 1994).

The "Fc region" can be a naturally-occurring or synthetic polypeptide that is homologous to the IgG C-terminal domain produced by digestion of IgG with papain. The polypeptide agents described herein can include the entire Fc region or a smaller portion that retains the ability to extend the circulating half-life of a chimeric polypeptide of which it is a part. In addition, and as noted, full-length or fragmented Fc regions can be variants of the wild-type molecule. That is, they can contain mutations that may or may not affect the function of the polypeptide; as described further below, native activity is not necessary or desired in all cases. In a preferred embodiment, the Fc region includes the hinge, CH2 and CH3 domains of human IgG1 or murine IgG2a.

The Fc region can be isolated from a naturally occurring source, recombinantly produced, or synthesized (as any polypeptide featured in the present invention can be). For example, an Fc region that is homologous to the IgG C-terminal domain can be produced by digestion of IgG with papain. The polypeptides of the invention can include the entire Fc region, or a smaller portion that retains the ability to lyse cells. In addition, full-length or fragmented Fc regions can be variants of the wild-type molecule. That is, they can contain mutations that may or may not affect the function of the polypeptide.

Chimeric AAT-Fc polypeptides can be constructed using no more than conventional molecular biological techniques, which are well within the ability of those of ordinary skill in the art to perform. As used herein, the terms "protein" and "polypeptide" both refer to any chain of amino acid residues, regardless of length or post-translational modification (e.g., glycosylation or phosphorylation).

To clone and express an AAT-Fc polypeptide one can, for example, subclone cDNA of AAT and an Fc region of an immunoglobulin into the pFUFC vector from InvivoGen to create an AAT-Fc fusion protein; the AAT-Fc portion of this plasmid can be cloned into the UCOE expression vector from Millipore; and stable human AAT expressed in CHO cells can be screened by ELISA. Large amounts of AAT fusion protein can be produced by the WAVE bioreactor system, and purification can be achieved with protein A affinity chromatography columns. The UCOE (ubiquitous chromatin opening element) expression system can be employed because it gives major improvements in gene expression in stably-transfected mammalian cells.

AAT activity can be measured in terms of the inhibitory capacity of AAT toward trypsin. Microplates can be coated with 1% of FBS and incubated for one hour. After a wash (3×) with $H_2O$, various concentrations of AAT can be incubated with a fixed amount of trypsin for 20 minutes at 37° C. in a 200 µl final reaction volume. A chromogenic substrate (L-pyroglutamylglycyl-L-arginine, p-nitroanilide hydrochloride) can then be added to the plate and incubation continued for about 5 minutes at room temperature. The reaction can be stopped with 50 µl of 50% acetic acid. Absorbance can be read at 400 nm in a microplate reader.

Nucleic Acid Molecules That Encode Agents of the Invention:

Polypeptide agents of the invention, including those that are fusion proteins (e.g., AAT-Fc, as discussed herein) cannot only be obtained by expression of a nucleic acid molecule in a suitable eukaryotic or prokaryotic expression system in vitro and subsequent purification of the polypeptide agent, but can also be administered to a patient by way of a suitable gene therapeutic expression vector encoding a nucleic acid molecule. Further, a nucleic acid can be introduced into a cell of a graft prior to transplantation of the graft. Thus, nucleic acid molecules encoding the agents described above are within the scope of the invention. Just as polypeptides of the invention can be described in terms of their identity with wild-type polypeptides, the nucleic acid molecules encoding them will necessarily have a certain identity with those that encode the corresponding wild-type polypeptides. For example, the nucleic acid molecule encoding a cytokine polypeptide is at least 65%, preferably at least 75%, more preferably at least 85%, and most preferably at least 90% (e.g., at least 90%, 91%, 92%, 93%, 94%, 95%, 96%, 97%, 98%, 99%, or 100%) identical to the nucleic acid encoding wild-type cytokine. For nucleic acids, the length of the sequences compared will generally be at least 50 nucleotides, preferably at least 60 nucleotides, more preferably at least 75 nucleotides, and most preferably 110 nucleotides.

The nucleic acid molecules that encode agents of the invention can contain naturally occurring sequences, or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

The nucleic acid molecules of the invention may be referred to as "isolated" when they are separated from either the 5' or the 3' coding sequence with which they are immediately contiguous in the naturally occurring genome of an organism. Thus, the nucleic acid molecules are not limited to sequences that encode polypeptides; some or all of the non-coding sequences that lie upstream or downstream from a coding sequence can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a RNA, molecules can be produced by in vitro transcription.

The isolated nucleic acid molecules of the invention can include fragments not found as such in the natural state. Thus, the invention encompasses recombinant molecules, such as those in which a nucleic acid sequence is incorporated into a vector (for example, a plasmid or viral vector) or into the genome of a heterologous cell (or the genome of a homologous cell, at a position other than the natural chromosomal location).

As described above, agents of the invention can be fusion proteins. In addition to, or in place of, the heterologous polypeptides described above, a nucleic acid molecule encoding an agent of the invention can contain sequences encoding a "marker" or "reporter." Examples of marker or reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT). As with many of the standard procedures associated with the practice of the invention, one of ordinary skill in the art will be aware of additional useful reagents, for example, of additional sequences that can serve the function of a marker or reporter.

The nucleic acid molecules described above can be contained within a vector that is capable of directing their expression in, for example, a cell that has been transduced with the vector. Accordingly, in addition to polypeptide agents, expression vectors containing a nucleic acid molecule encoding those agents and cells transfected with those vectors are among the preferred embodiments.

Vectors suitable for use in the present invention include T7-based vectors for use in bacteria (see, e.g., Rosenberg et al., *Gene* 56:125, 1987), the pMSXND expression vector for use in mammalian cells (Lee and Nathans, *J Biol Chem* 263:3521, 1988), yeast expression systems, such as *Pichia pastoris* (for example the PICZ family of expression vectors from Invitrogen, Carlsbad, Calif.) and baculovirus-derived vectors (for example the expression vector pBacPAK9 from Clontech, Palo Alto, Calif.) for use in insect cells. The nucleic acid inserts, which encode the polypeptide of interest in such vectors, can be operably linked to a promoter, which is selected based on, for example, the cell type in which expression is sought. For example, a T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. One of ordinary skill in the art is well aware of numerous promoters and other regulatory elements that can be used to direct expression of nucleic acids.

In addition to sequences that facilitate transcription of the inserted nucleic acid molecule, vectors can contain origins of replication, and other genes that encode a selectable marker. For example, the neomycin-resistance (neon) gene imparts G418 resistance to cells in which it is expressed, and thus permits phenotypic selection of the transfected cells. Other feasible selectable marker genes allowing for phenotypic selection of cells include various fluorescent proteins, e.g. green fluorescent protein (GFP) and variants thereof. Those of skill in the art can readily determine whether a given regulatory element or selectable marker is suitable for use in a particular experimental context.

Viral vectors that can be used in the invention include, for example, retroviral, adenoviral, and adeno-associated vectors, herpes virus, simian virus 40 (SV40), and bovine papilloma virus vectors (see, e.g., Gluzman (Ed.), Eukaryotic Viral Vectors, CSH Laboratory Press, Cold Spring Harbor, N.Y.).

Prokaryotic or eukaryotic cells that contain a nucleic acid molecule that encodes an agent of the invention and express the protein encoded in that nucleic acid molecule in vitro are also features of the invention. A cell of the invention is a transfected cell, i.e., a cell into which a nucleic acid molecule, for example a nucleic acid molecule encoding a polypeptide, has been introduced by means of recombinant DNA techniques. The progeny of such a cell are also considered within the scope of the invention. The precise components of the expression system are not critical. For example, a polypeptide can be produced in a prokaryotic host, such as the bacterium *E. coli*, or in a eukaryotic host, such as an insect cell (for example, Sf21 cells), or mammalian cells (e.g., COS cells, CHO cells, 293 cells, NIH 3T3 cells, or HeLa cells). These cells are available from many sources, including the American Type Culture Collection (Manassas, Va.). In selecting an expression system, it matters only that the components are compatible with one another. One of ordinary skill in the art is able to make such a determination. Furthermore, if guidance is required in selecting an expression system, one can consult Ausubel et al. (*Current Protocols in Molecular Biology*, John Wiley and Sons, New York, N.Y., 1993) and Pouwels et al. (*Cloning Vectors: A Laboratory Manual*, 1985 Suppl. 1987).

Eukaryotic cells that contain a nucleic acid molecule that encodes the agent of the invention and express the protein encoded in such nucleic acid molecule in vivo are also features of the invention.

Furthermore, eukaryotic cells of the invention can be cells that are part of a cellular transplant, a tissue or organ transplant. Such transplants can comprise either primary cells taken from a donor organism or cells that were cultured, modified and/or selected in vitro before transplantation to a recipient organism (e.g., eukaryotic cells lines, including stem cells or progenitor cells). Since, after transplantation into a recipient organism, cellular proliferation may occur, the progeny of such a cell are also considered within the scope of the invention. A cell, being part of a cellular, tissue or organ transplant, can be transfected with a nucleic acid encoding a polypeptide of interest and subsequently be transplanted into the recipient organism, where expression of the polypeptide occurs. Furthermore, such a cell can contain one or more additional nucleic acid constructs allowing for application of selection procedures, e.g. of specific cell lineages or cell types prior to transplantation into a recipient organism.

The expressed polypeptides can be purified from the expression system using routine biochemical procedures, and can be used as diagnostic tools or as therapeutic agents, as described below.

Production and Purification of Methionine-Rich Proteins

Production and purification of biologically active, methionine-rich proteins, including proteins such as AAT and AAT conjugated to an Fc region of an immunoglobulin, are difficult because the sulfur atom of methionine is easily oxidized and results in methionine sulfoxide or methionine sulfone. Oxidation of methionine results in a mixture of the two diastereomers, methionine-S-sulfoxide and methionine-R-sulfoxide. Oxidation of methionine residues on lead to less active polypeptides.

To reduce oxidation of methionine residues on proteins such as AAT and AAT conjugated to an Fc region of an immunoglobulin, growth media and purification and isolation reagents were supplemented with methionine and used to produce and isolate the proteins.

Provided herein are methods of producing methionine-rich proteins, e.g., AAT, AAT conjugated to an Fc region, or AAT conjugated to other protein(s), using special growth media, i.e., growth media that include high levels of methionine, e.g., a final concentration of at least 10 mM, e.g., at least 20 mM, 50 mM, 100 mM, 200 mM, or 500 mM, methionine. Also provided are methods of purifying and isolating active, methionine-rich proteins, e.g., AAT, AAT conjugated to an Fc region, or AAT conjugated to other protein(s), using special purification or isolation reagents, e.g., extraction buffers, wash buffers, and elution buffers, that are supplemented with methionine, e.g., to a final concentration of at least 10 mM, e.g., at least 20 mM, 50 mM, 100 mM, 200 mM, or 500 mM, methionine. The methods include providing a cell comprising a nucleic acid molecule encoding a polypeptide comprising AAT or AAT conjugated to an Fc region of an immunoglobulin or conjugated to other protein(s); and culturing the cell under conditions sufficient to produce AAT or AAT conjugated to an Fc region of an immunoglobulin or conjugated to other protein(s), e.g., in growth media having a concentration of at least 10 mM, e.g., at least 20 mM, 50 mM, 100 mM, 200 mM, or 500 mM, methionine, thereby producing AAT or AAT conjugated to an Fc region of an immunoglobulin or conjugated to other protein(s). The method may include purifying or isolating from the cell AAT or AAT conjugated to an Fc region or other protein(s) using at least one purification and/or isolation reagent having a concentration of at least 10 mM, e.g., at least 20 mM, 50 mM, 100 mM, 200 mM, or 500 mM, methionine. It will be appreciated that methods of the present invention can include growth of the cells in the methionine-rich medium and isolation using standard purification and/or isolation reagents. Alternatively, the methods can include growth of the cell in standard growth medium, followed by isolation using the special purification or isolation reagent(s), e.g., extraction buffers, wash buffers, and elution buffers, that are supplemented with methionine. In some instances, methods can be carried out using growth in methionine-rich medium followed by isolation using one or more special purification or isolation reagents that are supplemented with methionine.

Recombinant AAT-Fc Protein Expression

Human AAT-Fc plasmids can be transfected into the CHO-S Chinese hamster ovary cell line. AAT-Fc fusion proteins were expressed in a CHO cell line transfected with AAT-Fc plasmids. Transfected CHO cells were cultured in CD CHO medium (Gibco), a protein-free, serum-free medium, supplemented with 50 mM L-methionine. The proteins and purified by standard protein A chromatographic procedures using loading (pH 7) and elution (pH 2.1 to 3.2) conditions and the addition on 50 mM L-methionine to the wash, buffer, and elution media.

Stable clones are selected and subsequently subjected to selection for gene amplification. Stable clones that secrete soluble recombinant AAT-Fc can be grown in serum-free medium. Single cell clones can be selected and cultured. The culture medium is first filtered to remove debris. The filtrate can then be purified with protein A-conjugated beads that have been equilibrated with phosphate-buffered saline (PBS) containing 0.5 mol/L NaCl. The filtered cell culture medium can be passed through a column containing the protein A resin, and 1 mL fractions of purified protein collected. Glycine (pH 2.7) was used as the elution buffer, and the fractions were neutralized immediately with 100 μL of 1 mol/L Tris base with methionine.

Western Blotting

For the detection of recombinant AAT-Fc protein, aliquots of purified protein fractions can be analyzed by sodium dodecyl sulfate-polyacrylamide gel electrophoresis (SDS-PAGE) on 10% acrylamide gels. Resolved proteins can be transferred to a nitrocellulose membrane and Western blotting analysis performed using rabbit anti-human AAT (YbdY, Seoul Korea) and horse radish peroxidase-conjugated goat anti-human IgG Fc antibodies (Sigma-Aldrich, St. Louis, Mo., USA). Protein-antibody complexes can be detected using Supex (Neuronex, Seoul, Korea) and an LAS-4000 imaging device (Fujifilm, Japan).

Inhibitory Effect of AAT-Fc on the Enzymatic Activity of Elastase

The SENSOLYTE® Green Elastase Assay Kit (Anaspec, Inc., Fremont, Calif.) is a FRET-based assay that detects elastase activity. The kit provides an elastin, a natural substrate for elastases, labeled with 5-FAM fluorophore and QXL™ 520 quencher. Elastase-catalyzed hydrolysis yields brightly green fluorescence. An increase in fluorescence intensity is directly proportional to enzyme activity. Diminution of fluorescence intensity in the presence of AAT indicates elastase inhibition via AAT action. Activity was analyzed by a SPECTRAMAX M5® instrument (Molecular Devices, Sunnyvale, Calif.).

A no-acid condition refers to a commercial formulation of AAT used in the assay without any exposure to acidic pH. In acidic conditions, either a commercial formulation of AAT exposed to acidic conditions (e.g., pH 2.1) or an AAT-Fc fusion protein purified under acidic conditions will be assayed for elastase inhibition assay. Elastase is supplied in a commercial kit.

Pharmaceutical Compositions

Also described herein are pharmaceutical compositions, which include AAT conjugated to an Fc region of an immunoglobulin, e.g., where the AAT comprises a polypeptide that is at least 90%, 92%, 95%, 96%, 97%, 98%, 99%, or 100% identical to the amino acid sequence of SEQ ID NO:2 and the Fc region of the immunoglobulin comprises an amino acid sequence that is at least 90%, 92%, 95%, 96%, 97%, 98%, 99%, or 100% identical to SEQ ID NO:4 or 6, and vectors encoding an AAT conjugated to an Fc region of an immunoglobulin, e.g., wherein the nucleic acid sequence encoding AAT is at least 90%, 92%, 95%, 96%, 97%, 98%, 99%, or 100% identical to SEQ ID NO:1 and the nucleic acid sequence encoding the Fc region of the immunoglobulin is at least 90%, 92%, 95%, 96%, 97%, 98%, 99%, or 100% identical to SEQ ID NO:3 or 5. For example, a pharmaceutical composition can comprise a polypeptide comprising an amino acid sequence that is at least 90%, 92%, 95%, 96%, 97%, 98%, 99%, or 100% identical to SEQ ID NO:8, 10, 12, 14, 16, or 18, and a pharmaceutically acceptable carrier. In one aspect, pharmaceutical compositions comprise a vector comprising a nucleic acid molecule encoding a recombinant polypeptide comprising an AAT comprising an amino acid sequence that is at least 90%, 92%, 95%, 96%, 97%, 98%, 99%, or 100% identical to SEQ ID NO:2 conjugated to an Fc region of an immunoglobulin and a pharmaceutically acceptable carrier. In one embodiment, the nucleic acid molecule encoding AAT comprises a nucleic acid sequence that is at least 90%, 92%, 95%, 96%, 97%, 98%, 99%, or 100% identical to SEQ ID NO:1. In one embodiment, the nucleic acid molecule comprises an AAT-Fc nucleic acid sequence that is at least 90%, 92%, 95%, 96%, 97%, 98%, 99%, or 100% identical to SEQ ID NO:7, 9, 11, 13, 15, or 17.

Such compositions typically include the active compound and a pharmaceutically acceptable carrier. A "pharmaceutically acceptable carrier" can include one or more solvents, dispersion media, coatings, antibacterial and antifungal agents, isotonic and absorption delaying agents, and the like, compatible with pharmaceutical administration. Supplementary active compounds can also be incorporated into the compositions. The pharmaceutical compositions can be included in a container, pack, or dispenser together with instructions for administration.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, a polyol (for example, glycerol, propylene glycol, and liquid polyethylene glycol, and the like), or a suitable mixture thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be achieved by including an agent that delays absorption, e.g., aluminum monostearate or gelatin, in the composition.

Sterile injectable solutions can be prepared by incorporating the active compound in the required amount in an appropriate solvent with one or a combination of ingredients enumerated above, as required, followed by filtered sterilization. Typically, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Injectable compositions may contain various carriers such as vegetable oils, dimethylacetamide, dimethylformamide, ethyl lactate, ethyl carbonate, isopropyl myristate, ethanol, and polyols (glycerol, propylene glycol, liquid polyethylene glycol, and the like). For intravenous injections, the compounds may be administered by the drip method, whereby a pharmaceutical composition containing the active compound(s) and a physiologically acceptable excipient is infused. Physiologically acceptable excipients may include, for example, 5% dextrose, 0.9% saline, Ringer's solution or other suitable excipients. For intramuscular preparations, a sterile composition of a suitable soluble salt form of the compound can be dissolved and administered in a pharmaceutical excipient such as Water-for-Injection, 0.9% saline, or 5% glucose solution, or depot forms of the compounds (e.g., decanoate, palmitate, undecylenic, enanthate) can be dissolved in sesame oil.

Oral compositions typically include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Alternatively, the pharmaceutical composition can be formulated as a chewing gum, lollipop, or the like.

Liquid compositions for oral administration prepared in water or other aqueous vehicles can include solutions, emulsions, syrups, and elixirs containing, together with the active compound(s), wetting agents, sweeteners, coloring agents, and flavoring agents. Various liquid and powder compositions can be prepared by conventional methods for inhalation into the lungs of the patient to be treated.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Subjects Amenable to Treatment:

The compositions of the invention are useful in inhibiting T cells that are involved, or would be involved, in an immune response (e.g., a cellular immune response) to an antigen; in inhibiting other cells involved in the pathogenesis of immunological disorders (e.g., monocytes, macrophages, and other antigen presenting cells such as dendritic cells, NK cells, and granulocytes); and in destroying cells such as islet cells (as seen in diabetes), or hyperproliferating cells (as seen, for example, in tissues involved in immunological disorders such as synovial fibroblasts (which are affected in rheumatoid arthritis) keratinocytes (which are affected in psoriasis), or dermal fibroblasts (which are affected in systemic lupus erythematosus). Given these examples, other cell types that can usefully be targeted will be apparent to those of ordinary skill in the art.

Thus, the compositions of the invention can be used to treat patients who are suffering from, or at risk for, an immune disease, particularly autoimmune disease. Examples of autoimmune diseases suitable for treatment are Type 1 or Type 2 diabetes, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), irritable bowel disease (IBD), IgA neuropathy, juvenile arthritis, lichen planus, lupus erythematosus, Meniere's disease, mixed connective tissue disease, multiple sclerosis, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, rheumatoid arthritis, sarcoidosis, scleroderma, Sjogren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis.

Inflammatory conditions (which are often, but not always, associated with autoimmunity) which may be amenable to treatment are asthma, encephalitis, inflammatory bowel disease, chronic obstructive pulmonary disease (COPD), allergic disorders, pulmonary fibrosis, undifferentitated spondyloarthropathy, undifferentiated arthropathy, arthritis, inflammatory osteolysis, chronic inflammation resulting from chronic viral or bacterial infections, psoriasis (e.g., plaque psoriasis, pustular psoriasis, erythrodermic psoriasis, guttate psoriasis or inverse psoriasis).

Similarly, methods by which these agents are administered can be used to treat a patient who has received a transplant of synthetic or biological material, or a combination of both. Such transplants can be organ, tissue or cell transplants, or synthetic grafts seeded with cells, for example, synthetic vascular grafts seeded with vascular cells. In addition, patients suffering from GVHD or patients who have received a vascular injury would benefit from this method.

In particular, the compositions can be used to treat patients at risk for, or diagnosed with, Type 1 diabetes. The compositions are also useful for treating patients at risk for, or suffering from, Type 2 diabetes.

The invention encompasses administration of target-cell depleting forms of an agent that targets tissue destructive T cells, or inflammatory cells. With target-cell depleting forms of agents, it is possible to selectively kill autoreactive or "transplant destructive" immune cells without massive destruction of other subsets of T cells (e.g., regulatory T cells). Accordingly, the invention features a method of killing cells (e.g., autoreactive Th17 cells, or proinflammatory effector cells such as macrophages). These methods can be carried out by administering to a patient a combination of agents that includes an agent that activates the complement system, lyses cells by the ADCC mechanism, or otherwise kills cells expressing a selected target molecule.

While the present compositions and methods are clearly contemplated for use in human patients, the invention is not so limited. The compositions and methods can be used in veterinary settings as well (e.g., to treat a domesticated animal such as a dog, cat, or horse).

Formulations for Use and Routes of Administration:

Although agents of the present invention can be obtained from naturally occurring sources, they can also be synthesized or otherwise manufactured. Polypeptides that are derived from eukaryotic organisms or synthesized in E. coli, or other prokaryotes, and polypeptides that are chemically synthesized will be substantially free from their naturally associated components. In the event the polypeptide is a chimera, it can be encoded by a hybrid nucleic acid molecule containing one sequence that encodes all or part of the agent. Agents of the invention (e.g., polypeptides) can be fused to a hexa-histidine tag to facilitate purification of bacterially expressed protein, or to a hemagglutinin tag to facilitate purification of protein expressed in eukaryotic cells. Where polypeptides are recombinantly produced, codons can be optimized based on the codon preference of the host cell.

In therapeutic applications, agents of the invention can be administered with a physiologically acceptable carrier, such as physiological saline. The therapeutic compositions of the invention can also contain a carrier or excipient, many of which are known to one of ordinary skill in the art. Excipients that can be used include buffers (e.g., citrate buffer, phosphate buffer, acetate buffer, and bicarbonate buffer), amino acids, urea, alcohols, ascorbic acid, phospholipids, proteins (e.g., serum albumin), EDTA, sodium chloride, liposomes, mannitol, sorbitol, and glycerol. The agents of the invention can be formulated in various ways, according to the corresponding route of administration. For example, liquid solutions can be made for ingestion or injection; gels or powders can be made for ingestion, inhalation, or topical application. Methods for making such formulations are well known and can be found in, for example, "Remington's Pharmaceutical Sciences."

Routes of administration are also well known to skilled pharmacologists and physicians and include intraperitoneal, intramuscular, subcutaneous, and intravenous administration. Additional routes include intracranial (e.g., intracisternal or intraventricular), intraorbital, opthalmic, intracapsular, intraspinal, intraperitoneal, transmucosal, topical, subcutaneous, and oral administration. It is expected that the intravenous or intra-arterial routes will be preferred for the administration of polypeptide agents. The subcutaneous route may also be used frequently as the subcutaneous tissue provides a stable environment for polypeptides, from which they can be slowly released.

In case of cell-based therapies (gene therapies), the cells/tissues/organs could either be transfected by incubation, infusion or perfusion prior to transplantation with a nucleic acid composition, such that the therapeutic protein is expressed and subsequently released by the transplanted cells/tissues/organs within the recipient organism. As well, the cells/tissues/organs could undergo a pretreatment by perfusion or simple incubation with the therapeutic protein prior to transplantation in order to eliminate transplant-associated immune cells adherent to the donor cells/tissues/organs. In the case of cell transplants, the cells may be administered either by an implantation procedure or with a catheter-mediated injection procedure through the blood vessel wall. In some cases, the cells may be administered by release into the vasculature.

It is well known in the medical arts that dosages for any one patient depend on many factors, including the general health, sex, weight, body surface area, and age of the patient, as well as the particular compound to be administered, the time and route of administration, and other drugs being administered concurrently. Dosages for the polypeptide of the invention will vary, but can, when administered intravenously, be given in doses on the order of magnitude of 1 microgram to 10 mg/kg body weight or on the order of magnitude of 0.01 mg/l to 100 mg/l of blood volume. A dosage can be administered one or more times per day, if necessary, and treatment can be continued for prolonged periods of time. Determining the correct dosage for a given application is well within the abilities of one of ordinary skill in the art.

In all of the methods described herein, appropriate dosages of AAT-Fc can readily be determined by those of ordinary skill in the art of medicine, e.g., by monitoring the patient for signs of disease amelioration or inhibition, and increasing or decreasing the dosage and/or frequency of treatment as desired. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue to thereby, reduce side effects.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

For the AAT-Fc polypeptide described herein, an effective amount, e.g., of a protein or polypeptide (i.e., an effective dosage), ranges from about 0.001 to 30 mg/kg body weight, e.g., about 0.01 to 25 mg/kg body weight, e.g., about 0.1 to 20 mg/kg body weight. The protein or polypeptide can be administered one time per day, twice per day, one time per week, twice per week, for between about 1 to 52 weeks per year, e.g., between 2 to 50 weeks, about 6 to 40 weeks, or for about 4, 5, or 6 weeks. Skilled practitioners will appreciate that certain factors influence the dosage and timing required to effectively treat a patient, including but not limited to the type of patient to be treated, the severity of the disease or disorder, previous treatments, the general health and/or age of the patient, and other diseases present. Moreover, treatment of a patient with a therapeutically effective amount of a protein, polypeptide, nucleic acid, or other compound can include a single treatment or, preferably, can include a series of treatments.

When the AAT-Fc polypeptide described herein is to be administered to an animal (e.g., a human), a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Nucleic acid molecules (e.g., encoding an AAT-Fc fusion polypeptide) of the invention can be inserted into vectors and used as gene therapy vectors. Gene therapy vectors can be delivered to a subject by, for example, intravenous injection, local administration (see, e.g., U.S. Pat. No. 5,328, 470) or by stereotactic injection (see, e.g., Chen et al., *Proc Natl Acad Sci USA* 91:3054-3057, 1994). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

As noted here, subjects amenable to treatment include those that exhibit pancreatic β cell loss or functional insufficiency. These subjects, particularly when they also exhibit impaired glucose tolerance, are at risk of developing Type 1 diabetes or are at the inflection point between a diabetic and non-diabetic state. One of ordinary skill in the art will recognize that there is a progression of events associated with oncoming illness and that patients can be treated at varying points along the continuum. The compositions and methods described herein can also be used to treat subjects who are insulin resistant. Insulin resistant subjects include those who have Type 2 diabetes (a condition understood to be associated with insulin resistance), subjects who are at risk of developing Type 2 diabetes, and subjects diagnosed as having metabolic syndrome. The subjects also include insulin deficient patients with Type 1 diabetes, marginal islet function, and insulin resistance.

Models of Autoimmune Disease:

Models of autoimmune disease provide another means to assess combinations of the agents of the invention in vivo. These models are well known to those of ordinary skill in the art and can be used to determine whether a given combination of agents would be therapeutically useful in treating a specific autoimmune disease when delivered either directly, via genetic therapy, or via cell-based therapies.

Autoimmune diseases that have been modeled in animals include rheumatic diseases, such as rheumatoid arthritis and systemic lupus erythematosus (SLE), Type 1 diabetes, and autoimmune diseases of the thyroid, gut, and central nervous system. For example, animal models of SLE include MRL mice, BXSB mice, and NZB mice and their $F_1$ hybrids. These animals can be crossed in order to study particular aspects of the rheumatic disease process; progeny of the NZB strain develop severe lupus glomerulonephritis when crossed with NZW mice (Bielschowsky et al., *Proc. Univ. Otago Med. Sch.* 37:9, 1959; see also *Fundamental Immunology*, Paul, Ed., Raven Press, New York, N.Y., 1989). Similarly, a shift to lethal nephritis is seen in the progeny of NBZ X SWR matings (Data et al., *Nature* 263:412, 1976). The histological appearance of renal lesions in $SNF_1$ mice has been well characterized (Eastcott et al., *J Immunol* 131:2232, 1983; see also *Fundamental Immunology*, supra). Therefore, the general health of the animal as well as the histological appearance of renal tissue can be used to determine whether the administration of agents can effectively suppress the immune response in an animal model of SLE.

Animal models of intestinal inflammation are described, for example, by Elliott et al. (Elliott et al., 1998, Inflammatory Bowel Disease and Celiac Disease. In: The Autoimmune Diseases, Third ed., N. R. Rose and I. R. MacKay, eds. Academic Press, San Diego, Calif.). Some mice with genetically engineered gene deletions develop chronic bowel inflammation similar to IBD. See, e.g., Elson et al., *Gastroenterology* 109:1344, 1995; Berg et al., *J Clin Investigation* 98:1010, 1996; Ludviksson et al., *J Immunol* 158:104, 1997; and Mombaerts et al., *Cell* 75:274, 1993). These include mutant mice with targeted deletions for IL-2, IL-10, MHC class II or TCR genes among others.

One of the MRL strains of mice that develops SLE, MRL-lpr/lpr, also develops a form of arthritis that resembles rheumatoid arthritis in humans (Theofilopoulos et al., *Adv Immunol* 37:269, 1985). Alternatively, an experimental arthritis can be induced in rodents by injecting rat type II collagen (2 mg/ml) mixed 1:1 in Freund's complete adjuvant (100 µl total) into the base of the tail. Arthritis develops 2-3 weeks after immunization. The effectiveness of a candidate treatment is assessed by following the disease symptoms during the subsequent 2 weeks, as described by Chernajovsky et al. (*Gene Therapy* 2:731-735, 1995). Lesser symptoms, compared to control, indicate that the combined agents of the invention, and the nucleic acid molecules that encode them, function as immunosuppressants and are therefore useful in the treatment of immune disease, particularly autoimmune disease.

The ability of various combinations of agents to suppress the immune response in the case of Type 1 diabetes can be tested in the NOD mouse model discussed in the Examples, below, or in the BB rat strain, which was developed from a commercial colony of Wistar rats at the Bio-Breeding Laboratories in Ottawa. These rats spontaneously develop autoantibodies against islet cells and insulin, just as occurs with human Type 1 diabetes.

Autoimmune diseases of the thyroid have been modeled in the chicken. Obese strain (OS) chickens consistently develop spontaneous autoimmune thyroiditis resembling Hashimoto's disease (Cole et al., *Science* 160:1357, 1968). Approximately 15% of these birds produce autoantibodies to parietal cells of the stomach, just as in the human counterpart of autoimmune thyroiditis. The manifestations of the disease in OS chickens, which could be monitored in the course of any treatment regime, include body size, fat deposit, serum lipids, cold sensitivity, and infertility.

Models of autoimmune disease in the central nervous system (CNS) can also be experimentally induced. An inflammation of the CNS, which leads to paralysis, can be induced by a single injection of brain or spinal cord tissue with adjuvant in many different laboratory animals, including rodents and primates. This model, referred to as experimental allergic encephalomyelitis (EAE) is T cell mediated. Similarly, experimentally induced myasthenia gravis can be produced by a single injection of acetylcholine receptor with adjuvants (Lennon et al., *Ann. N.Y. Acad. Sci.* 274:283, 1976).

Islet Allograft Model:

DBA/2J islet cell allografts can be transplanted into rodents, such as 6-8 week-old B6 AF1 mice rendered diabetic by a single intraperitoneal injection of streptozotocin (225 mg/kg; Sigma Chemical Co., St. Louis, Mo.). As a control, syngeneic islet cell grafts can be transplanted into diabetic mice. Islet cell transplantation can be performed by following published protocols (for example, see Gotoh et al., *Transplantation* 42:3 87, 1986). Briefly, donor pancreata are perfused in situ with type IV collagenase (2 mg/ml; Worthington Biochemical Corp., Freehold, N.J.). After a 40-minute digestion period at 37° C., the islets are isolated on a discontinuous Ficoll gradient. Subsequently, 300-400 islets are transplanted under the renal capsule of each recipient. Allograft function can be followed by serial blood glucose measurements (ACCU-CHECK III™; Boehringer, Mannheim, Germany). Primary graft function is defined as a blood glucose level under 11.1 mmol/1 on day 3 post-transplantation, and graft rejection is defined as a rise in blood glucose exceeding 16.5 mmol/l (on each of at least two successive days) following a period of primary graft function.

EXAMPLES

The invention is further described in the following examples, which do not limit the scope of the invention described in the claims.

Example 1. Construction of Constructs 1 to 6

Figure 4:
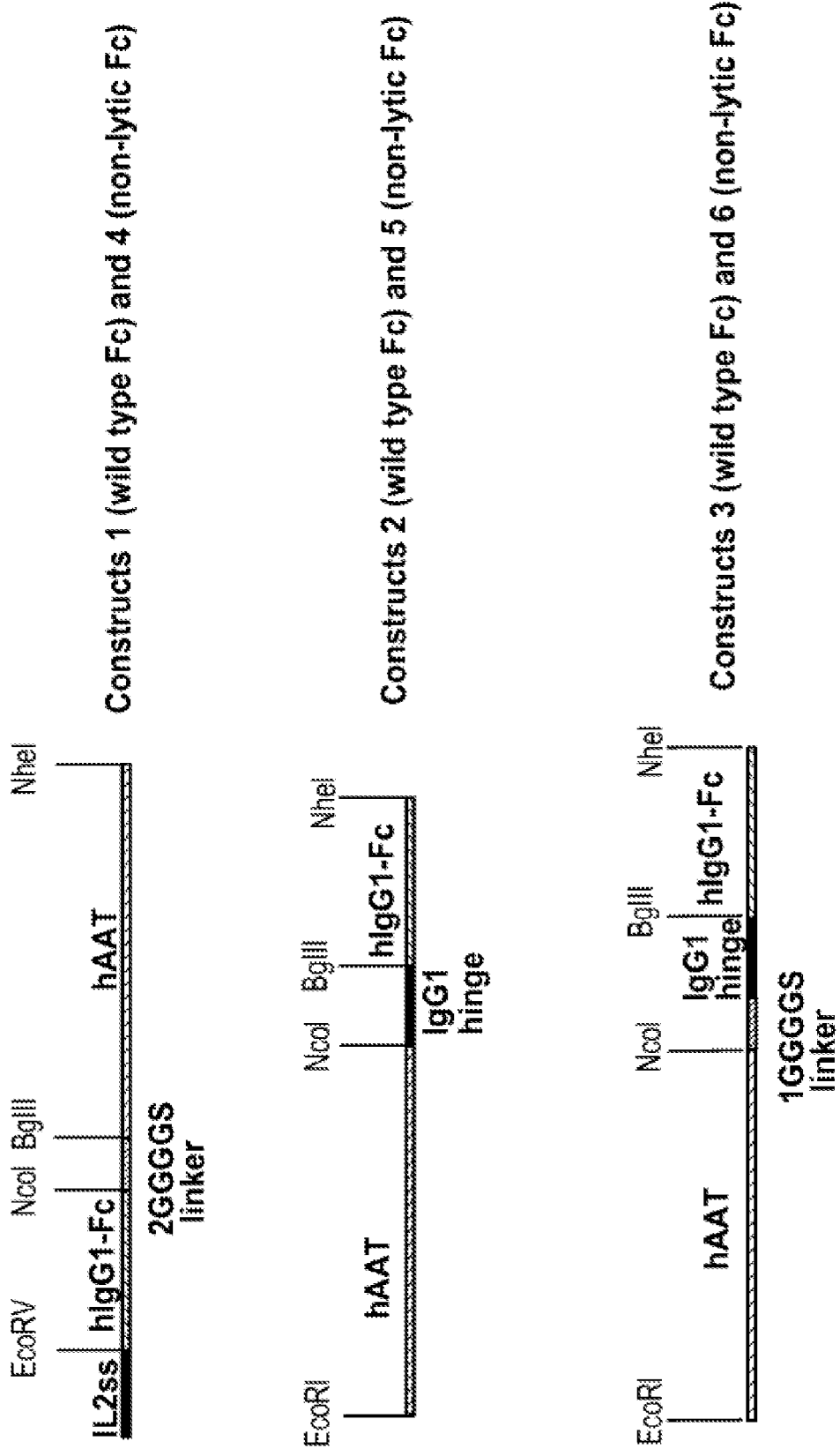
FIG. 4 is a schematic diagram of restriction sites in Constructs 1 to 6 used to integrate them into pFUSE expression vectors.

Constructs 1 and 4 were cloned in pFuse-hIgG-Fc2, and Constructs 2, 3, 5, and 6 were cloned in pFuse-hIgG-Fc1. For the generation of Constructs 4, 5, and 6, the wild type hIgG1-Fc sequence in pFuse vector backbone was replaced with a non-lytic hIgG1-Fc version. The non-lytic IgG1-Fc (with mutant residues: Leu-15-Glu; Glu-98-Ala; Cys-101-Ala; and Lys-102-Ala) was released from an earlier construct and cloned between EcoRV and NcoI in Construct 4 or between BglII and NheI in Constructs 5 and 6. In Construct 1, wild type hIgG1-Fc was cloned between EcoRV and NcoI. The IgG1 hinge and/or GGGGS linker sequences were cloned using annealed synthetic oligonucleotides between NcoI and BglII (FIG. 4).

Full length cDNA coding human AAT was amplified using cDNA clones available from Open Biosystems, using the following primers.

```
Primers
(5'-CCTTAGATCTATGCCGTCTTCTGTCTCGTGGGCATCC-3'
(SEQ ID NO: 19)
and

5'-CCTTGCTAGCTTATTTTTGGGTGGGATTCACCACTTTTCCC-3'
(SEQ ID NO: 20))
were used to clone hAAT in the Constructs 1 and 4.

Primers
(5'-CCTTGAATTCATGCCGTCTTCTGTCTCGTGGGCATCC-3'
(SEQ ID NO: 21)
and

5'-CCTTCCATGGTTTTTGGGTGGGATTCACCACTTTTCCC-3'
(SEQ ID NO: 22))
were used to clone hAAT in Constructs 2, 3, 5,
and 6.
```

Example 2. Methionine Protects AAT in Acidic Conditions

Figure 5A:
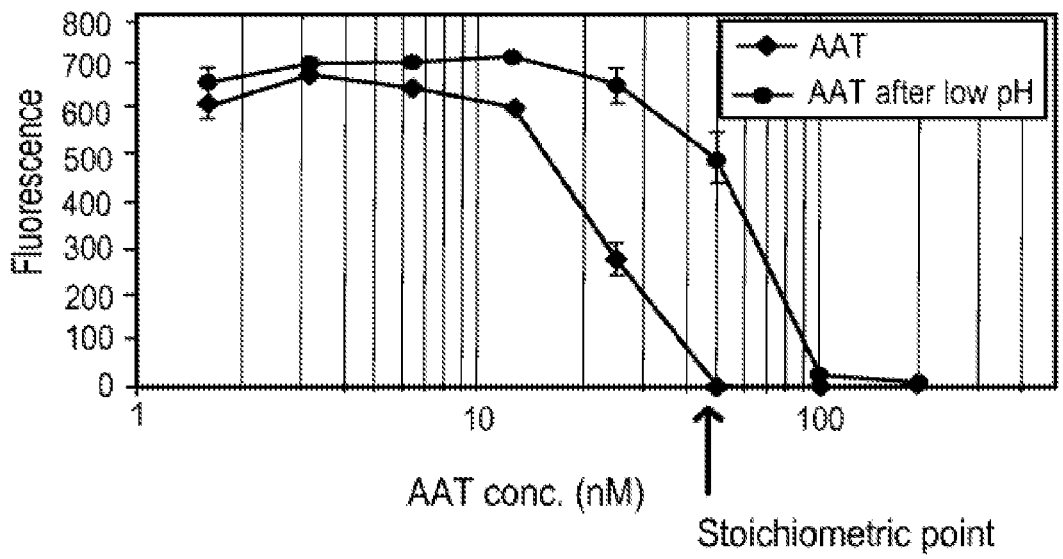
FIGS. 5A-5B are line graphs showing the stability of AAT in acidic conditions (pH 2.1).
Figure 5B:
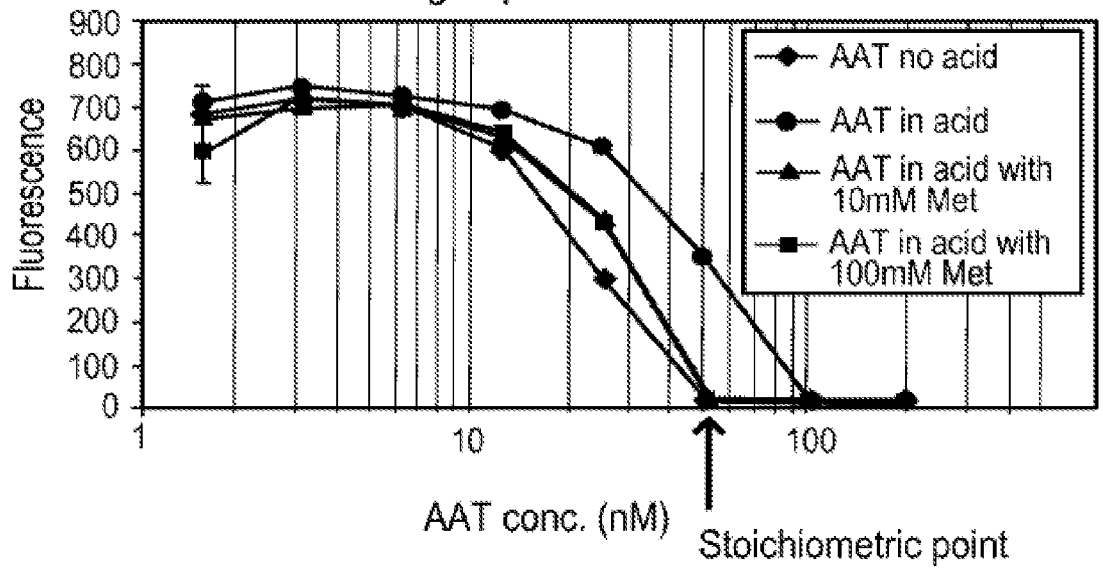

Exposure of AAT to acidic conditions, e.g., pH 2.1 for 20 minutes, results in an oxidized protein that is less active (FIG. 5A). However, L-methionine added to the growth media and/or purification reagents at 10 mM or 100 mM protected AAT from oxidation (FIG. 5B).

Figure 6:
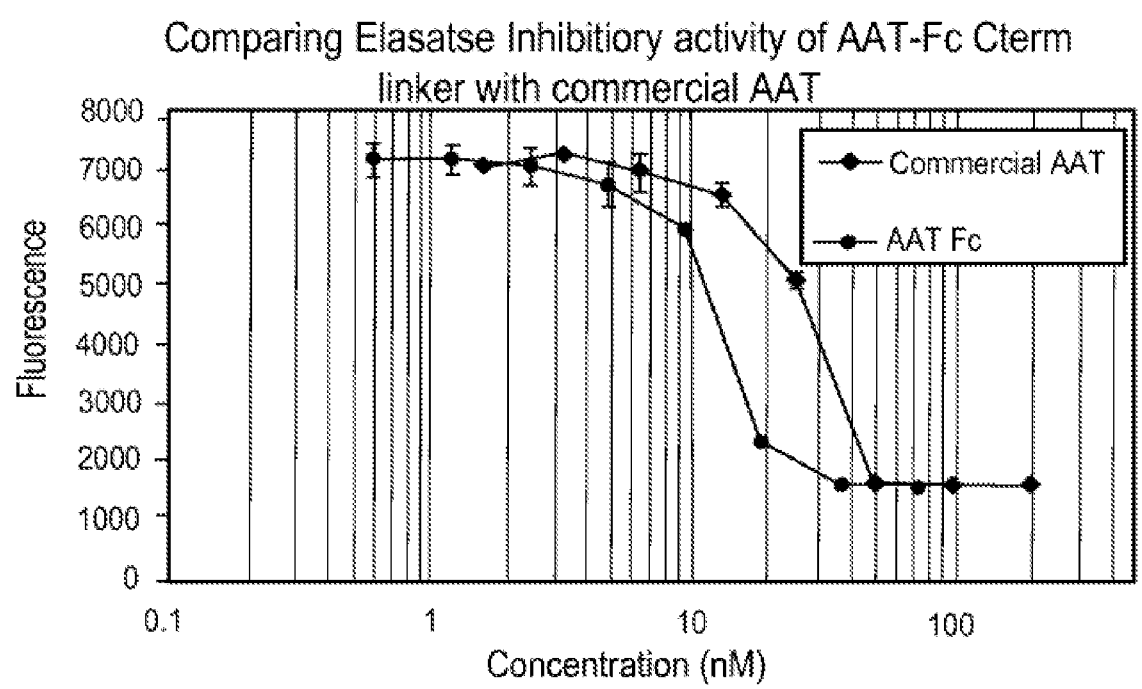
FIG. 6 is a line graph comparing elastase inhibitory activity of AAT-Fc Construct 2 (SEQ ID NO:10) with commercial AAT.

Example 3. AAT-Fc Construct 2 Inhibits Activity of Elastase Better Than Commercial AAT Increasing concentrations of AAT (either commercial AAT or AAT-Fc fusion protein) in the range of 1 to 200 nM were tested for the ability to inhibit elastase activity in a 96-well microtiter plate assay. Briefly, 40 µl of AAT and 10 µl of elastase solution were added to each well of a flat-bottom black 96-well microtiter plate, followed by the addition of 50 µl of the fluorescent substrate for elastase. Separate wells were maintained for test protein/inhibitor control, and enzyme and substrate controls were included. The contents of the wells were mixed for 30 seconds and incubated at room temperature for 30-60 minutes. At the end of the incubation period, the plate was read at Excitation/Emission: 490/520 nm (FIG. 6).

Figure 7A:
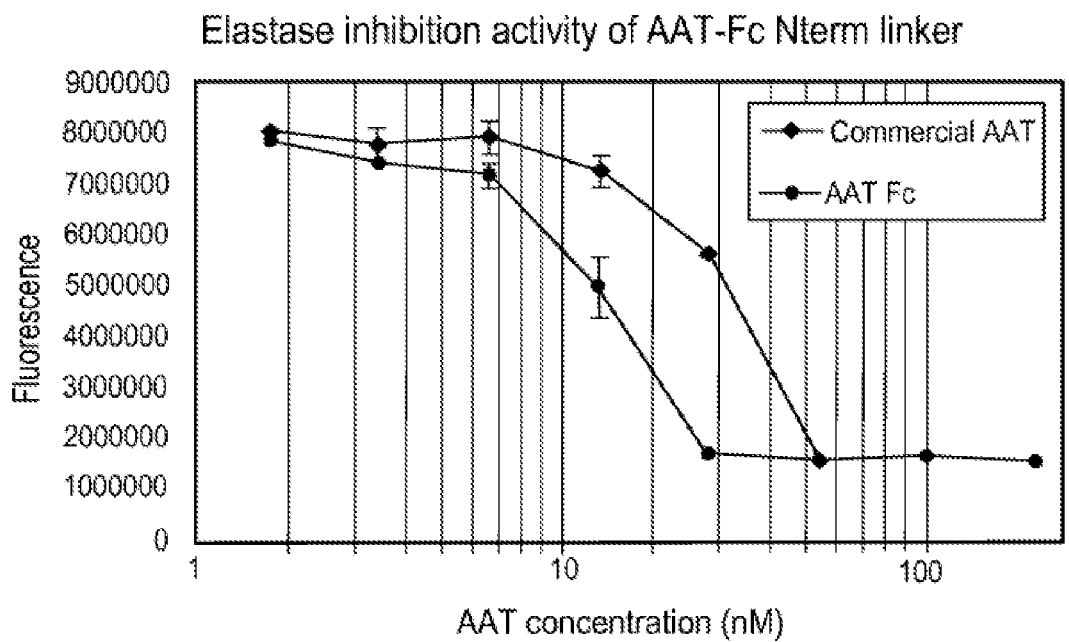
FIGS. 7A-7B are line graphs comparing elastase inhibitory activity of AAT-Fc Construct 1 (SEQ ID NO:8) with AAT-Fc Construct 3 (SEQ ID NO:12).
Figure 7B:
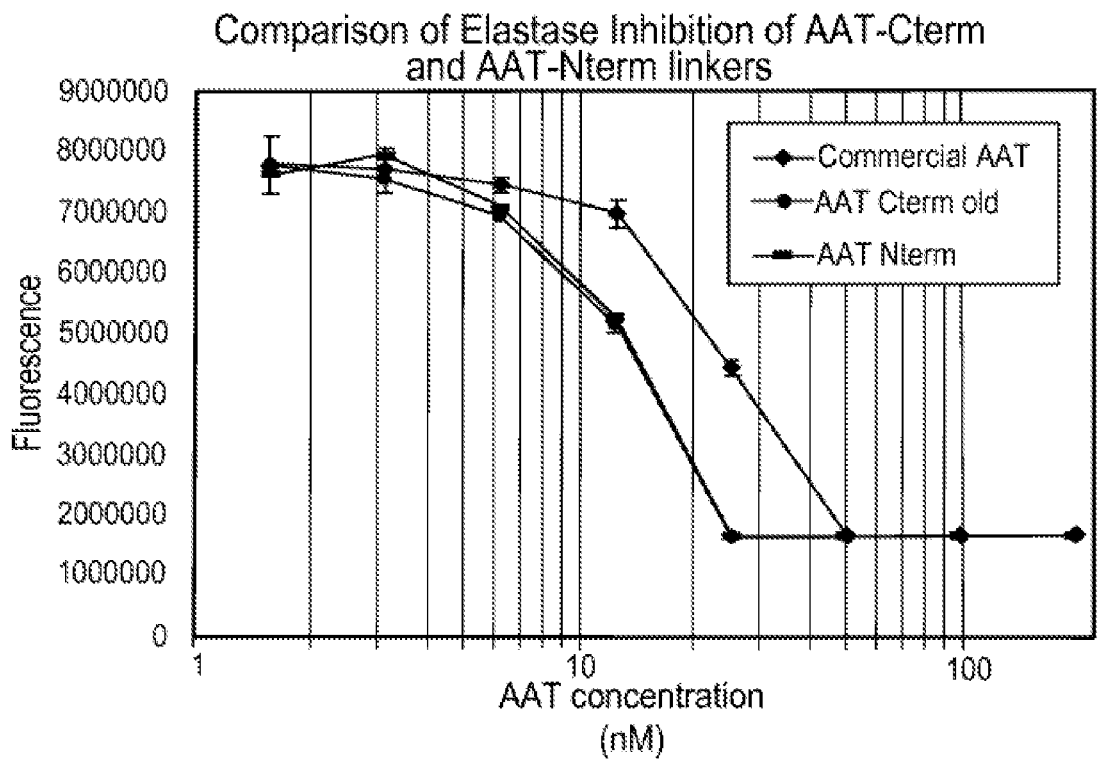

Example 4. AAT-Fc Constructs 1 and 3 Inhibit Activity of Elastase Better Than Commercial AAT The assay procedure was carried out as described above. In addition to testing the elastase inhibitory activity of commercial AAT, AAT-Fc fusion proteins generated using Constructs 1 and 3 carrying an N-terminal Fc or a C-terminal Fc fragment, respectively, were tested (FIGS. 7A-7B).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A recombinant polypeptide comprising an α1-antitrypsin polypeptide (AAT) conjugated to an Fc region of an immunoglobulin, wherein the polypeptide comprises an amino acid sequence selected from the group consisting of SEQ ID NOs: 8, 10, 12, 14, 16, and 18.

2. A nucleic acid molecule encoding a recombinant polypeptide comprising an α1-antitrypsin polypeptide (AAT) conjugated to an Fc region of an immunoglobulin, wherein the polypeptide comprises an amino acid sequence selected from the group consisting of SEQ ID NOs: 8, 10, 12, 14, 16, and 18.

3. The nucleic acid molecule of claim 2, wherein the nucleic acid molecule comprises a nucleic acid sequence selected from the group consisting of SEQ ID NOs: 7, 9, 11, 13, 15, and 17.

4. A cell comprising the nucleic acid molecule of claim 3.

5. A method of purifying a recombinant polypeptide comprising an AAT conjugated to an Fc region of an immunoglobulin, the method comprising:

providing the cell of claim 4;
culturing the cell under conditions sufficient to produce the recombinant polypeptide; and
purifying the recombinant polypeptide from the cell using a purification reagent comprising methionine.

6. The method of claim 5, wherein the cell is cultured in growth medium comprising at least 10 mM methionine.

7. The method of claim 5, wherein the purification reagent is selected from the group consisting of extraction buffer, wash buffer, and elution buffer.

8. The method of claim 5, wherein the purification reagent comprises at least 10 mM methionine.

9. A method of treating an autoimmune disease in a subject, the method comprising administering to the subject a therapeutically effective amount of a recombinant polypeptide comprising an AAT conjugated to an Fc region of an immunoglobulin, thereby treating the autoimmune disease in the subject, wherein the polypeptide comprises an amino acid sequence selected from the group consisting of SEQ ID NOs: 8, 10, 12, 14, 16, and 18.

10. The method of claim 9, wherein the autoimmune disease is Type 1 or Type 2 diabetes.

11. The method of claim 9, wherein the recombinant polypeptide is administered to the subject subcutaneously, intraperitoneally, intramusclularly, orally, or by infusion.

12. The method of claim 9, wherein the subject is human.

* * * * *

UNITED STATES PATENT AND TRADEMARK OFFICE
CERTIFICATE OF CORRECTION

PATENT NO. : 10,781,248 B2
APPLICATION NO. : 16/166990
DATED : September 22, 2020
INVENTOR(S) : Maria Koulmanda and Terry B. Strom Page 1 of 1

It is certified that error appears in the above-identified patent and that said Letters Patent is hereby corrected as shown below:

In the Claims

On Column 89, Line 5, in Claim 11, delete "intramusclularly," and insert -- intramuscularly, --, therefor.

Signed and Sealed this
Fourth Day of May, 2021

Drew Hirshfeld
*Performing the Functions and Duties of the
Under Secretary of Commerce for Intellectual Property and
Director of the United States Patent and Trademark Office*